United States Patent
Robinson et al.

(10) Patent No.: US 10,842,707 B2
(45) Date of Patent: Nov. 24, 2020

(54) MEDICAL DRAPE WITH PATTERN ADHESIVE LAYERS AND METHOD OF MANUFACTURING SAME

(71) Applicant: KCI Licensing, Inc., San Antonio, TX (US)

(72) Inventors: Timothy Mark Robinson, Basingstoke (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 185 days.

(21) Appl. No.: 14/080,348

(22) Filed: Nov. 14, 2013

(65) Prior Publication Data
US 2014/0155791 A1    Jun. 5, 2014

Related U.S. Application Data

(60) Provisional application No. 61/727,660, filed on Nov. 16, 2012.

(51) Int. Cl.
*A61F 13/02* (2006.01)
*A61H 9/00* (2006.01)
(Continued)

(52) U.S. Cl.
CPC .......... *A61H 9/0057* (2013.01); *A61B 46/40* (2016.02); *A61F 13/023* (2013.01);
(Continued)

(58) Field of Classification Search
CPC . B32B 37/12; B32B 37/0076; B32B 37/1292; A61B 46/00; A61B 46/20;
(Continued)

(56) References Cited

U.S. PATENT DOCUMENTS 1,355,846 A    10/1920  Rannells
1,944,834 A    1/1934   Bennett
(Continued)

FOREIGN PATENT DOCUMENTS

AU    550575 A1    3/1986
AU    550575 B2    3/1986
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
(Continued)

*Primary Examiner* — Anna K Kinsaul
*Assistant Examiner* — Camtu T Nguyen

(57) ABSTRACT

A medical drape for use with a reduced pressure system for providing reduced pressure to a tissue site is described. In some embodiments, the drape may include a flexible film, and an adhesive layer coupled to the flexible film. The adhesive layer may include a first adhesive disposed on a first portion of the flexible film in a first pattern. The first adhesive can be configured to secure the flexible film proximate to the tissue site. The adhesive layer generally includes a second adhesive disposed on a second portion of the flexible film in a second pattern. The second adhesive can be configured to seal the flexible film proximate to the tissue site. The first pattern and the second pattern are preferably registered so that the first portion and the second portion are offset to cover substantially different portions of the flexible film.

8 Claims, 10 Drawing Sheets

(51) Int. Cl.
*A61M 1/00* (2006.01)
*A61B 46/00* (2016.01)

(52) U.S. Cl.
CPC ........ *A61F 13/025* (2013.01); *A61F 13/0256* (2013.01); *A61F 13/0269* (2013.01); *A61F 13/0289* (2013.01); *A61M 1/0088* (2013.01)

(58) Field of Classification Search
CPC ......... A61B 46/23; A61B 46/27; A61B 46/30; A61B 19/08; A61B 19/088; A61B 2046/234; A61B 2046/236; A61B 2046/201; A61B 46/10; A61B 46/13; A61B 46/17; A61F 2013/00655; A61F 2013/00804; A61F 2013/00761; A61F 2013/0077; A61F 2013/00774; A61F 13/0246; A61F 13/025
USPC ................. 428/41.9; 156/291; 128/849–856; 602/54–56
See application file for complete search history.

(56) References Cited

U.S. PATENT DOCUMENTS

| | | |
|---|---|---|
| 2,547,758 A | 4/1951 | Keeling |
| 2,552,664 A | 5/1951 | Burdine |
| 2,632,443 A | 3/1953 | Lesher |
| 2,682,873 A | 7/1954 | Evans et al. |
| 2,860,081 A | 11/1958 | Eiken |
| 2,910,763 A | 11/1959 | Lauterbach |
| 2,969,057 A | 1/1961 | Simmons |
| 3,066,672 A | 12/1962 | Crosby, Jr. et al. |
| 3,172,808 A | 3/1965 | Baumann et al. |
| 3,183,116 A | 5/1965 | Schaar |
| 3,367,332 A | 2/1968 | Groves |
| 3,376,868 A | 4/1968 | Mondiadis |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,777,016 A | 12/1973 | Gilbert |
| 3,779,243 A | 12/1973 | Tussey et al. |
| 3,826,254 A | 7/1974 | Mellor |
| 3,852,823 A * | 12/1974 | Jones ..................... A42B 1/12 2/68 |
| 3,903,882 A | 9/1975 | Augurt |
| 3,967,624 A | 7/1976 | Milnamow |
| 3,983,297 A | 9/1976 | Ono et al. |
| 4,060,081 A | 11/1977 | Yannas et al. |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,163,822 A | 8/1979 | Walter |
| 4,165,748 A | 8/1979 | Johnson |
| 4,174,664 A | 11/1979 | Arnott et al. |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,323,069 A | 4/1982 | Ahr et al. |
| 4,333,468 A | 6/1982 | Geist |
| 4,343,848 A | 8/1982 | Leonard, Jr. |
| 4,360,015 A | 11/1982 | Mayer |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,414,970 A | 11/1983 | Berry |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,600,146 A | 7/1986 | Ohno |
| 4,605,399 A | 8/1986 | Weston et al. |
| 4,608,041 A | 8/1986 | Nielson |
| 4,617,021 A | 10/1986 | Leuprecht |
| 4,640,688 A | 2/1987 | Hauser |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,715,857 A | 12/1987 | Juhasz et al. |
| 4,733,659 A | 3/1988 | Edenbaum et al. |
| 4,743,232 A | 5/1988 | Kruger |
| 4,753,230 A | 6/1988 | Carus et al. |
| 4,758,220 A | 7/1988 | Sundblom et al. |
| 4,787,888 A | 11/1988 | Fox |
| 4,826,494 A | 5/1989 | Richmond et al. |
| 4,832,008 A | 5/1989 | Gilman |
| 4,838,883 A | 6/1989 | Matsuura |
| 4,840,187 A | 6/1989 | Brazier |
| 4,848,364 A | 7/1989 | Bosman |
| 4,863,449 A | 9/1989 | Therriault et al. |
| 4,871,611 A | 10/1989 | Lebel |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,930,997 A | 6/1990 | Bennett |
| 4,941,882 A | 7/1990 | Ward et al. |
| 4,953,565 A | 9/1990 | Tachibana et al. |
| 4,961,493 A | 10/1990 | Kaihatsu |
| 4,969,880 A | 11/1990 | Zamierowski |
| 4,981,474 A | 1/1991 | Bopp et al. |
| 4,985,019 A | 1/1991 | Michelson |
| 4,995,382 A | 2/1991 | Lang et al. |
| 4,996,128 A | 2/1991 | Aldecoa et al. |
| 5,010,883 A | 4/1991 | Rawlings et al. |
| 5,018,515 A | 5/1991 | Gilman |
| 5,025,783 A | 6/1991 | Lamb |
| 5,028,597 A | 7/1991 | Kodama et al. |
| 5,037,397 A | 8/1991 | Kalt et al. |
| 5,086,170 A | 2/1992 | Luheshi et al. |
| 5,092,323 A | 3/1992 | Riedel et al. |
| 5,092,858 A | 3/1992 | Benson et al. |
| 5,100,396 A | 3/1992 | Zamierowski |
| 5,112,323 A | 5/1992 | Winkler et al. |
| 5,127,601 A | 7/1992 | Schroeder |
| 5,134,994 A | 8/1992 | Say |
| 5,149,331 A | 9/1992 | Ferdman et al. |
| 5,151,314 A | 9/1992 | Brown |
| 5,152,757 A | 10/1992 | Eriksson |
| 5,167,613 A | 12/1992 | Karami et al. |
| 5,176,663 A | 1/1993 | Svedman et al. |
| 5,180,375 A | 1/1993 | Feibus |
| 5,215,522 A | 6/1993 | Page et al. |
| 5,232,453 A | 8/1993 | Plass et al. |
| 5,244,457 A | 9/1993 | Karami et al. |
| 5,246,775 A | 9/1993 | Loscuito |
| 5,261,893 A | 11/1993 | Zamierowski |
| 5,266,372 A * | 11/1993 | Arakawa ................. A61F 13/58 428/41.9 |
| 5,270,358 A | 12/1993 | Asmus |
| 5,278,100 A | 1/1994 | Doan et al. |
| 5,279,550 A | 1/1994 | Habib et al. |
| 5,298,015 A | 3/1994 | Komatsuzaki et al. |

(56) References Cited

U.S. PATENT DOCUMENTS

| | | |
|---|---|---|
| 5,342,329 A | 8/1994 | Croquevielle |
| 5,342,376 A | 8/1994 | Ruff |
| 5,344,415 A | 9/1994 | DeBusk et al. |
| 5,356,386 A | 10/1994 | Goldberg et al. |
| 5,358,494 A | 10/1994 | Svedman |
| 5,384,174 A | 1/1995 | Ward et al. |
| 5,387,207 A | 2/1995 | Dyer et al. |
| 5,419,769 A | 5/1995 | Devlin et al. |
| 5,423,778 A | 6/1995 | Eriksson et al. |
| 5,429,590 A | 7/1995 | Saito et al. |
| 5,437,622 A | 8/1995 | Carion |
| 5,437,651 A | 8/1995 | Todd et al. |
| 5,445,604 A | 8/1995 | Lang |
| 5,447,492 A | 9/1995 | Cartmell et al. |
| 5,458,938 A | 10/1995 | Nygard et al. |
| 5,501,212 A | 3/1996 | Psaros |
| 5,522,808 A | 6/1996 | Skalla |
| 5,527,293 A | 6/1996 | Zamierowski |
| 5,549,584 A | 8/1996 | Gross |
| 5,549,585 A | 8/1996 | Maher et al. |
| 5,556,375 A | 9/1996 | Ewall |
| 5,585,178 A * | 12/1996 | Calhoun .................. B32B 7/12 428/343 |
| 5,599,292 A | 2/1997 | Yoon |
| 5,607,388 A | 3/1997 | Ewall |
| 5,611,373 A | 3/1997 | Ashcraft |
| 5,634,893 A | 6/1997 | Rishton |
| 5,636,643 A | 6/1997 | Argenta et al. |
| 5,641,506 A | 6/1997 | Talke et al. |
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |
| 5,736,470 A | 4/1998 | Schneberger et al. |
| 5,759,570 A | 6/1998 | Arnold |
| 5,776,119 A | 7/1998 | Bilbo et al. |
| 5,807,295 A | 9/1998 | Hutcheon et al. |
| 5,830,201 A | 11/1998 | George et al. |
| 5,878,971 A | 3/1999 | Minnema |
| 5,902,439 A | 5/1999 | Pike et al. |
| 5,919,476 A | 7/1999 | Fischer et al. |
| 5,941,863 A | 8/1999 | Guidotti et al. |
| 5,964,252 A | 10/1999 | Simmons et al. |
| 5,981,822 A | 11/1999 | Addison |
| 5,998,561 A | 12/1999 | Jada |
| 6,071,267 A | 6/2000 | Zamierowski |
| 6,083,616 A | 7/2000 | Dressler |
| 6,086,995 A | 7/2000 | Smith |
| 6,135,116 A | 10/2000 | Vogel et al. |
| 6,174,306 B1 | 1/2001 | Fleischmann |
| 6,191,335 B1 | 2/2001 | Robinson |
| 6,201,164 B1 | 3/2001 | Wulff et al. |
| 6,228,485 B1 | 5/2001 | Leiter |
| 6,238,762 B1 | 5/2001 | Friedland et al. |
| 6,241,747 B1 | 6/2001 | Ruff |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 | 12/2002 | Carte et al. |
| 6,503,855 B1 | 1/2003 | Menzies et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,627,215 B1 | 9/2003 | Dale et al. |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 | 9/2004 | Gilman |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 7,070,584 B2 | 7/2006 | Johnson et al. |
| 7,154,017 B2 | 12/2006 | Sigurjonsson et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,298,197 B2 | 10/2012 | Eriksson et al. |
| 8,398,614 B2 | 3/2013 | Blott et al. |
| 8,449,509 B2 | 5/2013 | Weston |
| 8,529,532 B2 | 9/2013 | Pinto et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,632,523 B2 | 1/2014 | Eriksson et al. |
| 8,679,081 B2 | 3/2014 | Heagle et al. |
| 8,764,732 B2 | 7/2014 | Hartwell |
| 8,834,451 B2 | 9/2014 | Blott et al. |
| 8,920,830 B2 | 12/2014 | Mathies |
| 8,926,592 B2 | 1/2015 | Blott et al. |
| 9,017,302 B2 | 4/2015 | Vitaris et al. |
| 9,192,444 B2 | 11/2015 | Locke et al. |
| 9,198,801 B2 | 12/2015 | Weston |
| 9,211,365 B2 | 12/2015 | Weston |
| 9,289,542 B2 | 3/2016 | Blott et al. |
| 9,877,873 B2 | 1/2018 | Coulthard et al. |
| 9,956,120 B2 | 5/2018 | Locke |
| 2001/0030304 A1 | 10/2001 | Kohda et al. |
| 2001/0051178 A1 | 12/2001 | Blatchford et al. |
| 2002/0009568 A1 * | 1/2002 | Bries ..................... A47G 1/175 428/40.1 |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0090496 A1 * | 7/2002 | Kim ..................... B42D 5/003 428/201 |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0109855 A1 | 6/2003 | Solem et al. |
| 2003/0158577 A1 | 8/2003 | Ginn et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 | 2/2004 | Hunt et al. |
| 2004/0064132 A1 | 4/2004 | Boehringer et al. |
| 2004/0077984 A1 * | 4/2004 | Worthley .............. A61F 13/023 602/55 |
| 2004/0082925 A1 | 4/2004 | Patel |
| 2004/0099268 A1 | 5/2004 | Smith et al. |
| 2004/0118401 A1 | 6/2004 | Smith et al. |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0163278 A1 | 8/2004 | Caspers et al. |
| 2004/0186239 A1 | 9/2004 | Qin et al. |
| 2004/0219337 A1 * | 11/2004 | Langley ................. B32B 5/26 428/198 |
| 2004/0230179 A1 | 11/2004 | Shehada |

(56) References Cited

U.S. PATENT DOCUMENTS

| | | |
|---|---|---|
| 2005/0034731 A1* | 2/2005 | Rousseau ............ A61B 17/085 128/849 |
| 2005/0054998 A1 | 3/2005 | Poccia et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0158442 A1 | 7/2005 | Westermann et al. |
| 2005/0159695 A1 | 7/2005 | Cullen et al. |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2006/0014030 A1 | 1/2006 | Langen et al. |
| 2006/0020235 A1 | 1/2006 | Siniaguine |
| 2006/0079852 A1 | 4/2006 | Bubb et al. |
| 2006/0083776 A1 | 4/2006 | Bott et al. |
| 2006/0154546 A1 | 7/2006 | Murphy et al. |
| 2006/0236979 A1 | 10/2006 | Stolarz et al. |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0028526 A1 | 2/2007 | Woo et al. |
| 2007/0078366 A1 | 4/2007 | Haggstrom et al. |
| 2007/0161937 A1 | 7/2007 | Aali |
| 2007/0185426 A1 | 8/2007 | Ambrosio et al. |
| 2007/0190281 A1 | 8/2007 | Hooft |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2007/0283962 A1 | 12/2007 | Doshi et al. |
| 2008/0009812 A1 | 1/2008 | Riesinger |
| 2008/0027366 A1 | 1/2008 | Da Silva Macedo |
| 2008/0090085 A1 | 4/2008 | Kawate et al. |
| 2008/0119802 A1 | 5/2008 | Riesinger |
| 2008/0138591 A1 | 6/2008 | Graham et al. |
| 2008/0149104 A1 | 6/2008 | Eifler |
| 2008/0173389 A1 | 7/2008 | Mehta et al. |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2009/0025724 A1 | 1/2009 | Herron, Jr. |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216168 A1 | 8/2009 | Eckstein |
| 2009/0216170 A1 | 8/2009 | Robinson et al. |
| 2009/0216204 A1 | 8/2009 | Bhavaraju et al. |
| 2009/0227969 A1 | 9/2009 | Jaeb et al. |
| 2009/0234306 A1 | 9/2009 | Vitaris |
| 2009/0234307 A1 | 9/2009 | Vitaris |
| 2009/0264807 A1 | 10/2009 | Haggstrom et al. |
| 2009/0292264 A1 | 11/2009 | Hudspeth et al. |
| 2009/0312662 A1 | 12/2009 | Colman et al. |
| 2009/0326487 A1 | 12/2009 | Vitaris |
| 2009/0326488 A1 | 12/2009 | Budig et al. |
| 2010/0028390 A1 | 2/2010 | Cleary et al. |
| 2010/0030170 A1 | 2/2010 | Keller et al. |
| 2010/0063467 A1 | 3/2010 | Addison et al. |
| 2010/0106106 A1 | 4/2010 | Heaton et al. |
| 2010/0106118 A1 | 4/2010 | Heaton et al. |
| 2010/0125259 A1 | 5/2010 | Olson |
| 2010/0159192 A1 | 6/2010 | Cotton |
| 2010/0168633 A1 | 7/2010 | Bougherara et al. |
| 2010/0168635 A1 | 7/2010 | Freiding et al. |
| 2010/0185163 A1 | 7/2010 | Heagle |
| 2010/0212768 A1 | 8/2010 | Resendes |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0268144 A1 | 10/2010 | Lu et al. |
| 2010/0286582 A1 | 11/2010 | Simpson et al. |
| 2010/0305490 A1 | 12/2010 | Coulthard et al. |
| 2010/0305524 A1 | 12/2010 | Vess et al. |
| 2010/0318072 A1 | 12/2010 | Johnston et al. |
| 2010/0324516 A1 | 12/2010 | Braga et al. |
| 2011/0046585 A1 | 2/2011 | Weston |
| 2011/0054423 A1 | 3/2011 | Blott et al. |
| 2011/0118683 A1 | 5/2011 | Weston |
| 2011/0137271 A1 | 6/2011 | Andresen et al. |
| 2011/0160686 A1 | 6/2011 | Ueda et al. |
| 2011/0171480 A1 | 7/2011 | Mori et al. |
| 2011/0172617 A1 | 7/2011 | Riesinger |
| 2011/0201984 A1 | 8/2011 | Dubrow et al. |
| 2011/0224631 A1 | 9/2011 | Simmons et al. |
| 2011/0229688 A1 | 9/2011 | Cotton |
| 2011/0244010 A1 | 10/2011 | Doshi |
| 2011/0257612 A1 | 10/2011 | Locke et al. |
| 2011/0257617 A1 | 10/2011 | Franklin |
| 2011/0281084 A1 | 11/2011 | Ashwell |
| 2011/0282309 A1 | 11/2011 | Adie et al. |
| 2012/0016322 A1 | 1/2012 | Coulthard et al. |
| 2012/0019031 A1 | 1/2012 | Bessert |
| 2012/0036733 A1 | 2/2012 | Dehn |
| 2012/0040131 A1 | 2/2012 | Speer |
| 2012/0059339 A1 | 3/2012 | Gundersen |
| 2012/0095380 A1 | 4/2012 | Gergely et al. |
| 2012/0109034 A1 | 5/2012 | Locke et al. |
| 2012/0123359 A1 | 5/2012 | Reed |
| 2012/0143157 A1 | 6/2012 | Riesinger |
| 2012/0237722 A1 | 9/2012 | Seyler et al. |
| 2012/0258271 A1 | 10/2012 | Maughan |
| 2012/0310186 A1 | 12/2012 | Moghe et al. |
| 2013/0030394 A1 | 1/2013 | Locke et al. |
| 2013/0053746 A1 | 2/2013 | Roland et al. |
| 2013/0066285 A1 | 3/2013 | Locke et al. |
| 2013/0096518 A1 | 4/2013 | Hall et al. |
| 2013/0098360 A1 | 4/2013 | Hurmez et al. |
| 2013/0116661 A1 | 5/2013 | Coward et al. |
| 2013/0150763 A1 | 6/2013 | Mirzaei et al. |
| 2013/0152945 A1 | 6/2013 | Locke et al. |
| 2013/0165887 A1 | 6/2013 | Mitchell et al. |
| 2013/0172843 A1 | 7/2013 | Kurata |
| 2013/0189339 A1 | 7/2013 | Vachon |
| 2013/0261585 A1 | 10/2013 | Lee |
| 2013/0304007 A1 | 11/2013 | Toth |
| 2013/0330486 A1 | 12/2013 | Shields |
| 2014/0039423 A1 | 2/2014 | Riesinger |
| 2014/0039424 A1 | 2/2014 | Locke |
| 2014/0058309 A1 | 2/2014 | Addison et al. |
| 2014/0107561 A1 | 4/2014 | Dorian et al. |
| 2014/0107562 A1 | 4/2014 | Dorian et al. |
| 2014/0141197 A1 | 5/2014 | Hill et al. |
| 2014/0155849 A1 | 6/2014 | Heaton et al. |
| 2014/0163491 A1 | 6/2014 | Schuessler et al. |
| 2014/0171851 A1 | 6/2014 | Addison |
| 2014/0178564 A1 | 6/2014 | Patel |
| 2014/0309574 A1 | 10/2014 | Cotton |
| 2014/0336557 A1 | 11/2014 | Durdag et al. |
| 2014/0350494 A1 | 11/2014 | Hartwell et al. |
| 2014/0352073 A1 | 12/2014 | Goenka |
| 2015/0030848 A1 | 1/2015 | Goubard |
| 2015/0045752 A1 | 2/2015 | Grillitsch et al. |
| 2015/0057625 A1 | 2/2015 | Coulthard |
| 2015/0080788 A1 | 3/2015 | Blott et al. |
| 2015/0080815 A1 | 3/2015 | Chakravarthy et al. |
| 2015/0119830 A1 | 4/2015 | Luckemeyer et al. |
| 2015/0119833 A1 | 4/2015 | Coulthard et al. |
| 2015/0141941 A1 | 5/2015 | Allen et al. |
| 2015/0190286 A1 | 7/2015 | Allen et al. |
| 2015/0290041 A1 | 10/2015 | Richard |

(56) References Cited

U.S. PATENT DOCUMENTS

| | | | |
|---|---|---|---|
| 2016/0000610 A1 | 1/2016 | Riesinger | |
| 2016/0067107 A1 | 3/2016 | Cotton | |
| 2016/0144084 A1 | 5/2016 | Collinson et al. | |

FOREIGN PATENT DOCUMENTS

| | | | |
|---|---|---|---|
| AU | 745271 | | 4/1999 |
| AU | 755496 | | 2/2002 |
| AU | 745271 | B2 | 3/2002 |
| AU | 755496 | B2 | 12/2002 |
| AU | 2009200608 | A1 | 10/2009 |
| CA | 2005436 | | 6/1990 |
| CA | 2005436 | A1 | 6/1990 |
| CN | 87101823 | A | 8/1988 |
| DE | 26 40 413 | A1 | 3/1978 |
| DE | 43 06 478 | A1 | 9/1994 |
| DE | 29 504 378 | U1 | 9/1995 |
| DE | 295 04 378 | U1 | 10/1995 |
| DE | 202004018245 | U1 | 7/2005 |
| DE | 202014100383 | U1 | 2/2015 |
| EP | 097517 | A1 | 1/1984 |
| EP | 0100148 | A1 | 2/1984 |
| EP | 0117632 | A2 | 9/1984 |
| EP | 0147119 | A2 | 7/1985 |
| EP | 0161865 | A2 | 11/1985 |
| EP | 0251810 | A2 | 1/1988 |
| EP | 0275353 | A2 | 7/1988 |
| EP | 0358302 | A2 | 3/1990 |
| EP | 0538917 | A1 | 4/1993 |
| EP | 0630629 | A1 | 12/1994 |
| EP | 0659390 | A2 | 6/1995 |
| EP | 0633758 | B1 | 10/1996 |
| EP | 1002846 | A1 | 5/2000 |
| EP | 1018967 | A1 | 7/2000 |
| EP | 1018967 | B1 | 8/2004 |
| EP | 2578193 | A1 | 4/2013 |
| GB | 692578 | | 6/1953 |
| GB | 692578 | A | 6/1953 |
| GB | 1386800 | A | 3/1975 |
| GB | 2 195 255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 329 127 | B | 3/1999 |
| GB | 2 333 965 | A | 8/1999 |
| GB | 2377939 | A | 1/2003 |
| GB | 2392836 | A | 3/2004 |
| GB | 2393655 | A | 4/2004 |
| GB | 2425487 | A | 11/2006 |
| GB | 2452720 | A | 3/2009 |
| GB | 2496310 | A | 5/2013 |
| JP | 1961003393 | | 2/1961 |
| JP | S62139523 | U | 9/1987 |
| JP | S62-275456 | A | 11/1987 |
| JP | 4129536 | | 4/1992 |
| JP | 2005205120 | A | 8/2005 |
| JP | 2007254515 | A | 10/2007 |
| JP | 2008080137 | A | 4/2008 |
| JP | 4129536 | B2 | 8/2008 |
| SG | 71559 | | 4/2002 |
| WO | 80/02182 | | 10/1980 |
| WO | 87/04626 | | 8/1987 |
| WO | 8707164 | A1 | 12/1987 |
| WO | 90/010424 | | 9/1990 |
| WO | 93/09727 | | 5/1993 |
| WO | 94/020041 | | 9/1994 |
| WO | 96/05873 | | 2/1996 |
| WO | 9622753 | A1 | 8/1996 |
| WO | 97/18007 | | 5/1997 |
| WO | 99/13793 | | 3/1999 |
| WO | 99/65542 | A1 | 12/1999 |
| WO | 01019306 | A1 | 3/2001 |
| WO | 01/36188 | A1 | 5/2001 |
| WO | 01/60296 | A1 | 8/2001 |
| WO | 0168021 | A1 | 9/2001 |
| WO | 0185248 | | 11/2001 |
| WO | 0185248 | A1 | 11/2001 |
| WO | 0190465 | A2 | 11/2001 |
| WO | 01085248 | | 11/2001 |
| WO | 01085248 | A1 | 11/2001 |
| WO | 0243743 | A1 | 6/2002 |
| WO | 02062403 | A1 | 8/2002 |
| WO | 03-018098 | A2 | 3/2003 |
| WO | 03045294 | A1 | 6/2003 |
| WO | 03045492 | A1 | 6/2003 |
| WO | 03053484 | A1 | 7/2003 |
| WO | 2004024197 | A1 | 3/2004 |
| WO | 2004037334 | A1 | 5/2004 |
| WO | 2004112852 | A1 | 12/2004 |
| WO | 2005002483 | A2 | 1/2005 |
| WO | 2005062896 | A2 | 7/2005 |
| WO | 2005105176 | A1 | 11/2005 |
| WO | 2005123170 | A1 | 12/2005 |
| WO | 2007022097 | A2 | 2/2007 |
| WO | 2007030601 | A2 | 3/2007 |
| WO | 2007070269 | A1 | 6/2007 |
| WO | 2007085396 | A1 | 8/2007 |
| WO | 2007087811 | A1 | 8/2007 |
| WO | 2007113597 | A2 | 10/2007 |
| WO | 2007133618 | A2 | 11/2007 |
| WO | 2008026117 | A1 | 3/2008 |
| WO | 2008041926 | A1 | 4/2008 |
| WO | 2008048527 | A2 | 4/2008 |
| WO | 2008054312 | A1 | 5/2008 |
| WO | 2008/082444 | A2 | 7/2008 |
| WO | 2008100440 | A1 | 8/2008 |
| WO | 2008104609 | A1 | 9/2008 |
| WO | 2008/131895 | A1 | 11/2008 |
| WO | 2009/002260 | A1 | 12/2008 |
| WO | 2008149107 | A1 | 12/2008 |
| WO | 2009066105 | A1 | 5/2009 |
| WO | 2009066106 | A1 | 5/2009 |
| WO | 2009081134 | A1 | 7/2009 |
| WO | 2009089016 | A1 | 7/2009 |
| WO | 2009/124100 | A1 | 10/2009 |
| WO | 2009126103 | A1 | 10/2009 |
| WO | 2010011148 | A1 | 1/2010 |
| WO | 2010016791 | A1 | 2/2010 |
| WO | 2010032728 | A1 | 3/2010 |
| WO | 2010/056977 | A2 | 5/2010 |
| WO | 2010129299 | A2 | 11/2010 |
| WO | 2011008497 | A2 | 1/2011 |
| WO | 2011/049562 | A1 | 4/2011 |
| WO | 2011043786 | A1 | 4/2011 |
| WO | 2011115908 | A1 | 9/2011 |
| WO | 2011121127 | A1 | 10/2011 |
| WO | 2011130570 | A1 | 10/2011 |
| WO | 2011162862 | A1 | 12/2011 |
| WO | 2012/112204 | A1 | 8/2012 |
| WO | 2012104584 | A1 | 8/2012 |
| WO | 2012140378 | A1 | 10/2012 |
| WO | 2012143665 | A1 | 10/2012 |
| WO | 2013009239 | A1 | 1/2013 |
| WO | 2013090810 | A1 | 6/2013 |
| WO | 2014022400 | A1 | 2/2014 |
| WO | 2014039557 | A1 | 3/2014 |
| WO | 2014/113253 | A1 | 7/2014 |
| WO | 2014140608 | A1 | 9/2014 |
| WO | 2014143488 | A1 | 9/2014 |
| WO | 2015/065615 | A1 | 5/2015 |
| WO | 2015130471 | A1 | 9/2015 |
| WO | 2017048866 | A1 | 3/2017 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/the British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for Pot International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).
International Search Report and Written Opinion for corresponding PCT/US2013/070070, dated Jan. 29, 2014.
International Search Report and Written Opinion for PCT/US20131070070 dated Jan. 29, 2014.
International Search Report and Written Opinion for PCT/GB2008/003075 dated Mar. 11, 2010.
International Search Report and Written Opinion for PCT/GB2008/004216 dated Jul. 2, 2009.
International Search Report and Written Opinion for PCT/GB2012/000099 dated May 2, 2012.
EP Examination Report dated May 22, 2014 for EP.
International Search Report and Written Opinion for PCT/US2012/069893 dated Apr. 8, 2013.
International Search Report and Written Opinion for PCT/US2014/016320 dated Apr. 15, 2014.
International Search Report and Written Opinion for PCT/US2014/056566 dated Dec. 5, 2014.
International Search Report and Written Opinion for PCT/US2014/056508 dated Dec. 9, 2014.
International Search Report and Written Opinion for PCT/US2014/056524 dated Dec. 11, 2014.
International Search Report and Written Opinion for PCT/US2014/056594 dated Dec. 2, 2014.
Partial Internationl Search Report dated Jul. 31, 2009; PCT Internationl Application No. PCT/US2009/036222.
International Search Report and Written opinion dated Dec. 15, 2009; PCT Internation Application No. PCT/US2009/036222.
International Search Report and Written Opinion dated Feb. 24, 2010; PCT/US2009/057182.
International Search Report and Written Opinion dated Jan. 5, 2010; PCT International Application No. PCT/US2009/057130.
Response filed Oct. 20, 2011 for U.S. Appl. No. 12/398,904.
Interview Summary dated Oct. 27, 2011 for U.S. Appl. No. 12/398,904.

(56) References Cited

OTHER PUBLICATIONS

Non-Final Office Action dated Jul. 20, 2011 for U.S. Appl. No. 12/398,904.
V.A. Solovev et al., Guidelines, The Method of Treatment of Immagure External Fistulas in the Upper Gastrointestinal Tract, editor-in-chief Prov. V.I. Parahonyak (S.M. Kirov Gorky State Medican Institute, Gorky, U.S.S.R. 1987) ("Solovev Guidelines").
V.A. Kuznetsov & N.A. Bagautdinov, "Vacuum and Vacuum-Sorption Treatement of Open Septic Wounds," in All-Union Conference on Wounds and Wound Infections: Presentation Abstracts, edited by B.M. Kostyuchenok et al. (Mosco, U. S.S.R. Oct. 28-29, 1986) pp. 91-92 ("Bagautdinov II").
V.A. Solovev, Dissertation Abstract, Treatement and Prevention of Suture Failures after Gastric Resection (S.M. Kirov Gorky State Medical Institute, Gorky, U.S.S.R. 1998 ("Solovev Abstract").
NDP 1000 Negative Pressure Wound Terapy System, Kalypto Medical, pp. 1-4.
Partial International Search Report dated Jul. 31, 2009 for PCT International Application No. PCT/US2009/036217.
International Search Report and Written Opinion dated May 31, 2010 for PCT Application No. PCT/US2009/064364.
Examination report for AU2009221772 dated Apr. 4, 2013.
Response filed Oct. 21, 2011 for U.S. Appl. No. 12/398,891.
Interview Summary dated Oct. 27, 2011 for U.S. Appl. No. 12/398,891.
Restriction Requirement dated Jun. 13, 2011 for U.S. Appl. No. 12/398,891.
Response filed Jun. 24, 2011 for U.S. Appl. No. 12/398,891.
Non-Final Office Action dated Jul. 21, 2011 for U.S. Appl. No. 12/398,891.
International Search Report and Written Opinion dated Oct. 19, 2010; PCT International Application No. PCT/US2009/036217.
International Search Report and Written Opinion dated Feb. 24, 2010; PCT International Application No. PCT/US2009/057182.
NPD 1000 Negative Pressure Would Therapy System, Kalypto Medical, pp. 1-4.
Partial International Search Report dated Jul. 31, 2009; PCT Internationl Application No. PCT/US2009/036222.
Non-Final Rejection for U.S. Appl. No. 12/398,904 dated Mar. 14, 2012.
Response to Non-Final Rejection for U.S. Appl. No. 12/398,904, filed Jun. 4, 2012.
International Search Report and Written Opinion for PCT/US2014/061251 dated May 8, 2015.
International Search Report and Written Opinion for PCT/IB2013/060862 dated Jun. 26, 2014.
International Search Report and Written Opinion for corresponding PCT application PCT/US2016/051768 dated Dec. 15, 2016.
International Search Report and Written Opinion for PCT/US2015/015493 dated May 4, 2015.
European Search Report for corresponding Application No. 15194949.2.
European Search Report for corresponding EPSN 15157408.4 published on Sep. 30, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion for PCT/US2015/029037 dated Sep. 4, 2015.
International Search Report and Written Opinion dated Jun. 1, 2011 for PCT International Application No. PCT/US2011/028344.
European Search Report for EP 11714148.1, dated May 2, 2014.
European Search Report for corresponding Application No. 15192606.0 dated Feb. 24, 2016.
International Search Report and Written Opinion for corresponding PCT/US2014/048081 dated Nov. 14, 2014.
International Search Report and Written Opinion for corresponding PCT/US2014/010704 dated Mar. 25, 2014.
European Examination Report dated Jun. 29, 2016, corresponding to EP Application No. 16173614.5.
European Search Report for corresponding EP Application 171572787 dated Jun. 6, 2017.
International Search Report and Written Opinion for corresponding application PCT/US2016/031397.
Japanese office action for corresponding application 2015-547246, dated Sep. 5, 2017.
Office Action for related U.S. Appl. No. 13/982,650, dated Dec. 14, 2017.
Australian Office Action for related application 2013344686, dated Nov. 28, 2017.
Office Action for related U.S. Appl. No. 14/517,521, dated Dec. 12, 2017.
Office Action for related U.S. Appl. No. 14/490,898, dated Jan. 4, 2018.
International Search Report and Written Opinion for related appplication PCT/US2017/058209, dated Jan. 10, 2018.
Office Action for related U.S. Appl. No. 14/965,675, dated Jan. 31, 2018.
International Search Report and Written Opinion for related application PCT/US2016/047351, dated Nov. 2, 2016.
M. Waring et al., "Cell attachment to adhesive dressing: qualitative and quantitative analysis", Wounds, UK, (2008), vol. 4, No. 3, pp. 35-47.
R. White, "Evidence for atraumatic soft silicone wound dressing use". Wound, UK (2005), vol. 3, pp. 104-108, Mepilex Border docs, (2001).
European Search Report for corresponding application 17183683.6, dated Sep. 18, 2017.
European Search Report for corresponding application 17164033.7, dated Oct. 13, 2017.
Extended European Search Report for corresponding application 17191970.7, dated Oct. 26, 2017.
Office Action for related U.S. Appl. No. 14/965,675, dated Aug. 9, 2018.
Office Action for related U.S. Appl. No. 15/307,472, dated Oct. 18, 2018.
Extended European Search Report for related application 17177013.4, dated Mar. 19, 2018.
Extended European Search Report for related application 16793298.7, dated Mar. 27, 2018.
Office Action for related U.S. Appl. No. 15/314,426, dated Aug. 29, 2019.
Office Action for related U.S. Appl. No. 15/410,991, dated May 2, 2019.
Office Action for related U.S. Appl. No. 14/965,675, dated Dec. 12, 2018.
Office Action for related U.S. Appl. No. 14/619,714, dated Dec. 3, 2018.
Office Action for related U.S. Appl. No. 14/630,290, dated Jan. 11, 2019.
Office Action for related U.S. Appl. No. 15/265,718, dated Feb. 7, 2019.
Extended European Search Report for related application 18193559.4, dated Dec. 17, 2018.
Office Action for related U.S. Appl. No. 15/600,451, dated Nov. 27, 2019.
Australian Office Action for related application 2018278874, dated Feb. 12, 2020.
Office Action for related U.S. Appl. No. 14/630,290, dated Apr. 30, 2020.
Office Action for related U.S. Appl. No. 15/793044, dated May 13, 2020.
EP Informal Search Report for related Application No. 191866003, received May 11, 2020.
Office Action for related U.S. Appl. No. 15/884,198, dated May 19, 2020.
Office Action for related U.S. Appl. No. 16/007,060, dated Aug. 18, 2020.
Office Action for related U.S. Appl. No. 15/937,485, dated Aug. 4, 2020.

(56) References Cited

OTHER PUBLICATIONS

Office Action for related U.S. Appl. No. 15/793,044, dated Sep. 24, 2020.
Extended European Search Report for related application 20185730.7, dated Oct. 9, 2020.

* cited by examiner

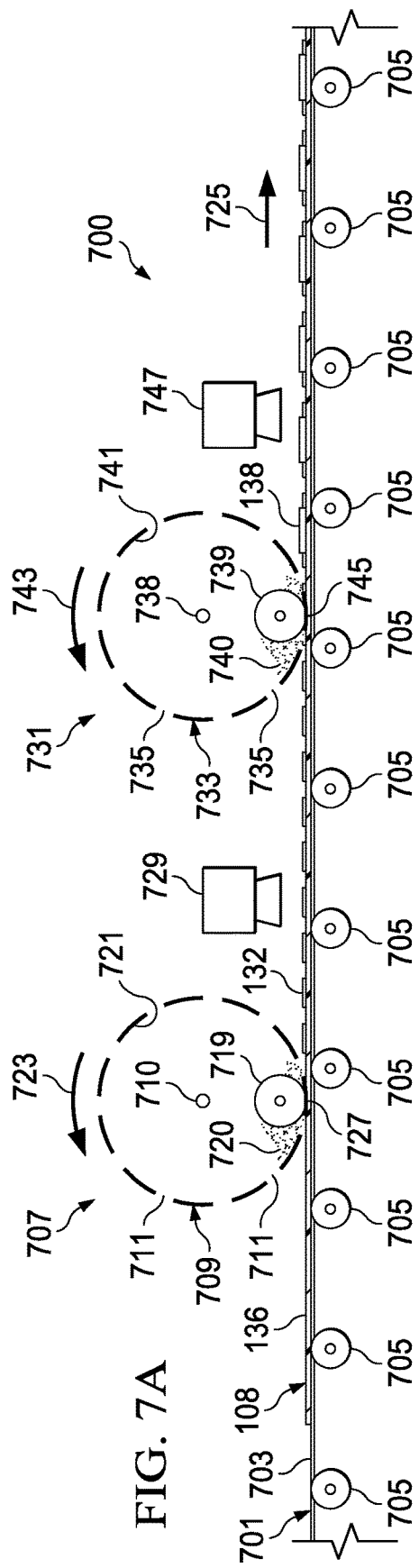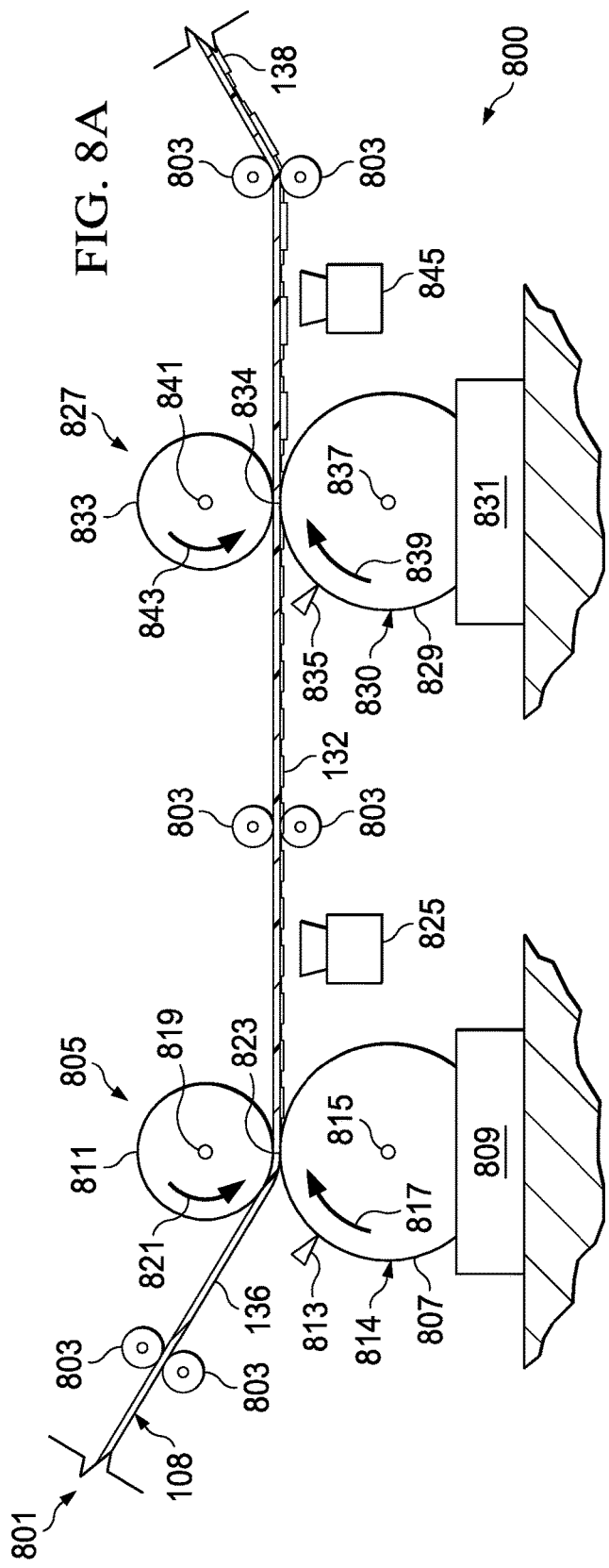

MEDICAL DRAPE WITH PATTERN ADHESIVE LAYERS AND METHOD OF MANUFACTURING SAME

The present invention claims the benefit, under 35 USC § 119(e), of the filing of U.S. Provisional Patent Application Ser. No. 61/727,660, entitled "Medical Drape with Pattern Adhesive Layers and Method of Manufacturing Same," filed Nov. 16, 2012, by Locke et al., which is incorporated herein by reference for all purposes.

FIELD

The present disclosure relates generally to dressings for adhering to a patient, and more particularly, but without limitation to, a medical drape having patterned adhesive layers deposited thereon and methods to manufacture the same.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure is commonly referred to as "reduced-pressure therapy," but may also be known by other names, including "negative pressure wound therapy" and "vacuum therapy," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of reduced-pressure therapy are widely known, the cost and complexity of reduced-pressure therapy can be a limiting factor in its application, and the development and operation of reduced-pressure systems, components, and processes continues to present significant challenges to manufacturers, healthcare providers, and patients.

SUMMARY

According to an illustrative, non-limiting embodiment, a medical drape is described. The medical drape may include a flexible film and a first adhesive disposed on a first portion of the flexible film in a first pattern. The medical drape may also include a second adhesive disposed on a second portion of the flexible film in a second pattern. The second pattern may be registered with the first pattern so that the first portion and the second portion cover substantially different portions of the flexible film.

According to another illustrative embodiment, a system for treating a tissue site with reduced pressure is described. The system may include a manifold for distributing reduced pressure proximate to a tissue site and a reduced-pressure source fluidly coupled to the manifold. The system may also include a drape. The drape may include a first adhesive and a second adhesive coupled to the drape. The second adhesive may be registered with the first adhesive so that the first adhesive and the second adhesive cover substantially different portions of the drape.

According to yet another illustrative embodiment, a method of manufacturing a medical drape is disclosed. The method provides a flexible film and disposes a first adhesive on a side of the flexible film in a first pattern. The method also disposes a second adhesive on the side of the flexible film in a second pattern. The first adhesive and the second adhesive cover substantially different portions of the flexible film. The second adhesive may have a tackiness less than a tackiness of the first adhesive.

According to still another illustrative embodiment, a method for treating a tissue site with reduced pressure is disclosed. The method disposes a manifold for distributing reduced pressure proximate to a tissue site and fluidly couples a reduced-pressure source to the manifold. The method disposes a medical drape over the tissue site. The medical drape may have a first adhesive and a second adhesive coupled to the medical drape. The second adhesive may be registered with the first adhesive so that the first and second adhesives cover substantially different portions of the medical drape. The method applies the second adhesive to the tissue site to form a sealing coupling between the drape and the tissue site. The method positions the drape. The method applies a force to the first adhesive to form a bonding coupling between the drape and the tissue site.

Other aspects, features, and advantages of the illustrative embodiments will become apparent with reference to the drawings and detailed description that follow.

BRIEF DESCRIPTION OF THE DRAWINGS

Illustrative embodiments are described in detail below with reference to the attached drawings, which are incorporated by reference herein, and wherein:

FIG. 7A is a schematic diagram of an illustrative screen apparatus for manufacturing the medical drape of FIG. 2;

FIG. 8A is a schematic diagram of an illustrative transfer apparatus for manufacturing the medical drape of FIG. 2;

DETAILED DESCRIPTION

New and useful systems, methods, and apparatuses associated with medical drapes used for regulating pressure are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

Figure 1:
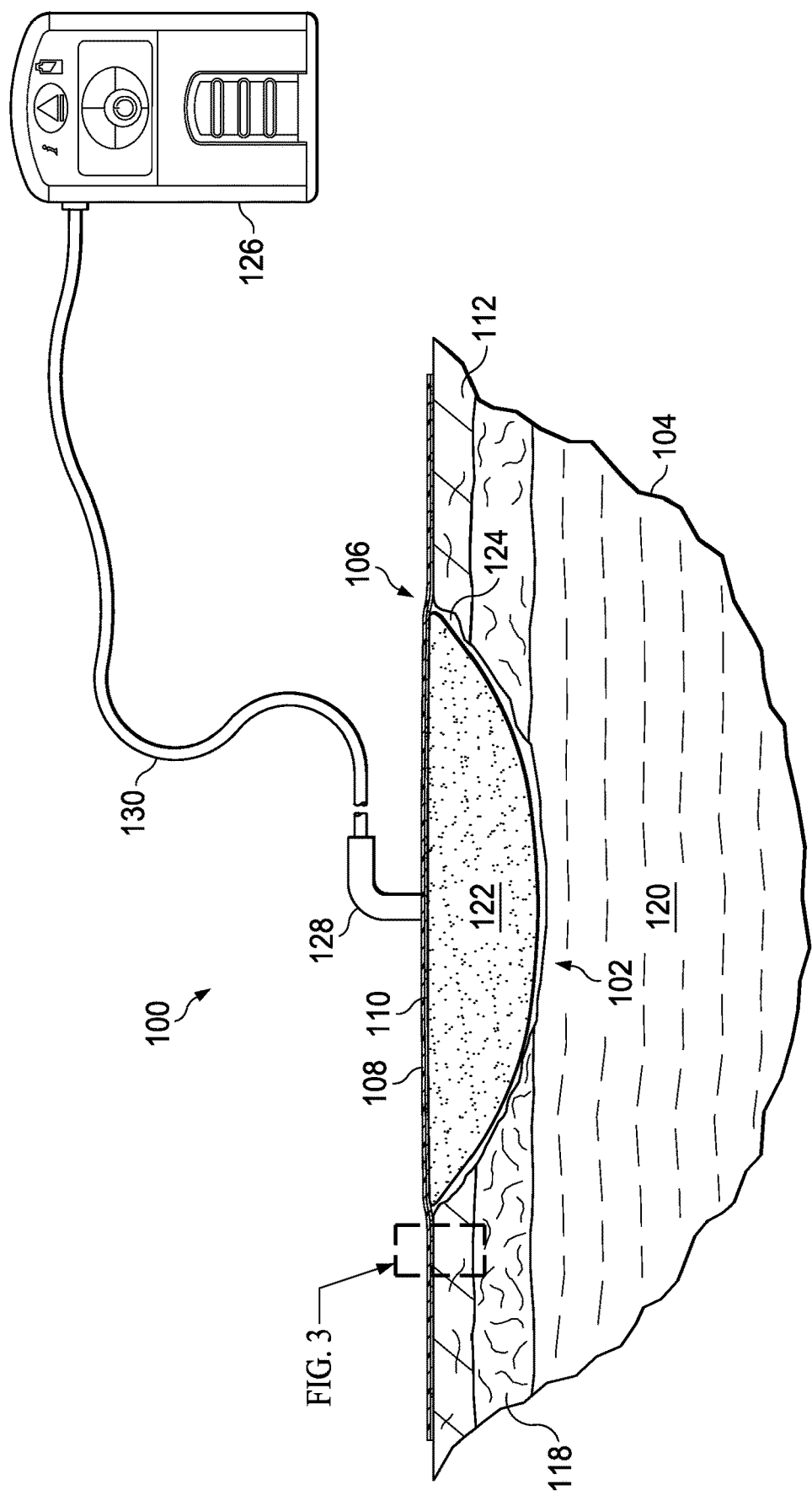
FIG. 1 is a schematic, diagram (with a portion shown in elevation) of an illustrative embodiment of a system for treating a tissue site on a patient with reduced pressure that may be associated with some illustrative embodiments of the system.

FIG. 1 is a sectional view of a system 100 for treating a tissue site 102 with a reduced pressure illustrating details that may be associated with some embodiments. The system 100 may include a drape, such as a medical drape 106, which may be attached to an epidermis 112. The medical drape 106 can substantially prevent the leakage of fluids while allowing vapor to egress through medical drape 106. The medical drape 106 can maintain an adequately strong mechanical connection to the epidermis 112 during operation, but may be detached with minimal or substantially reduced pain.

In general, components of the reduced-pressure therapy system 100 may be coupled directly or indirectly. For example, the reduced-pressure source 126 may be directly coupled to the reduced-pressure interface 128 and indirectly coupled to the tissue site 102 through the reduce-pressure interface 128. Components may be fluidly coupled to each other to provide a path for transferring fluids (i.e., liquid and/or gas) between the components. In some embodiments, components may be fluidly coupled with a tube, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, a tissue interface, such as the manifold 122, may be placed within, over, on, against, or otherwise adjacent to a tissue site. For example, the manifold 122 may be placed against a tissue site, and the medical drape 106 may be placed over the manifold 122 and sealed to tissue proximate to the tissue site. Tissue proximate to a tissue site is often undamaged epidermis peripheral to the tissue site. Thus, the drape 108 can provide a sealed therapeutic environment 124 proximate to the tissue site. The sealed therapeutic environment 124 may be substantially isolated from the external environment, and the reduced-pressure source 126 can reduce the pressure in the sealed therapeutic environment 124. Reduced pressure applied uniformly through the tissue interface in the sealed therapeutic environment 124 can induce macrostrain and microstrain in the tissue site, as well as remove exudates and other fluids from the tissue site. The removed exudates and other fluids can be collected in a container and disposed of properly.

The fluid mechanics of using a reduced-pressure source to reduce pressure in another component or location, such as within a sealed therapeutic environment 124, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

In general, exudates and other fluids flow toward lower pressure along a fluid path. This orientation is generally presumed for purposes of describing various features and components of reduced-pressure therapy systems herein. Thus, in the context of reduced-pressure therapy, the term "downstream" typically implies something in a fluid path relatively closer to a reduced-pressure source, and conversely, the term "upstream" implies something relatively further away from a reduced-pressure source. Similarly, it may be convenient to describe certain features in terms of fluid "inlet" or "outlet" in such a frame of reference. However, a fluid path may also be reversed in some applications, such as by substituting a positive-pressure source, and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of tissue that are not necessarily wounded or defective, but are instead areas in which it may be desired to add or promote the growth of additional tissue. For example, reduced pressure may be used in certain tissue areas to grow additional tissue that may be harvested and transplanted to another tissue location. In some embodiments, the tissue site 102 may be a wound that extends through the epidermis 112, through a dermis 118, and into subcutaneous tissue 120.

"Reduced pressure" generally refers to a pressure less than a local ambient pressure, such as the ambient pressure in a local environment external to a sealed therapeutic environment 124 provided by the medical drape 106. In many cases, the local ambient pressure may also be the atmospheric pressure in a patient's vicinity. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

A reduced-pressure source, such as the reduced-pressure source 126, may be a reservoir of air at a reduced pressure, or may be a manual or electrically-powered device that can reduce the pressure in a sealed volume, such as a vacuum pump, a suction pump, a wall-suction port available at many healthcare facilities, or a micro-pump, for example. A reduced-pressure source may be housed within or used in conjunction with other components, such as sensors, processing units, alarm indicators, memory, databases, software, display devices, or operator interfaces that further facilitate reduced-pressure therapy. While the amount and nature of reduced pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

A tissue interface, such as the manifold 122, can generally be adapted to contact a tissue site or other layers of a dressing, such as the medical drape 106. A tissue interface may be partially or fully in contact with a tissue site. If a tissue site is a wound, for example, a tissue interface may partially or completely fill the wound, or may be placed over the wound. A tissue interface may take many forms, and may be many sizes, shapes, or thicknesses depending on a variety of factors, such as the type of treatment being implemented or the nature and size of a tissue site. For example, the size and shape of a tissue interface may be adapted to the contours of deep and irregular shaped tissue sites.

Generally, a manifold, such as the manifold 122, for example, is a substance or structure adapted to distribute or remove fluids from a tissue site. A manifold may include flow channels or pathways that can distribute fluids provided to and removed from a tissue site. In one illustrative embodiment, the flow channels or pathways may be interconnected to improve distribution of fluids provided to or removed from a tissue site. For example, a manifold may be an open-cell foam, porous tissue collection, and other porous material such as gauze or felted mat that generally includes structural elements arranged to form flow channels. Liquids, gels, and other foams may also include or be cured to include flow channels.

In one illustrative embodiment, the manifold 122 may be a porous foam pad having interconnected cells adapted to distribute reduced pressure across a tissue site. The foam material may be either hydrophobic or hydrophilic. In one non-limiting example, the manifold 122 may be reticulated polyurethane foam such as GranuFoam® dressing available from Kinetic Concepts, Inc. of San Antonio, Tex.

In some embodiments, such as embodiments in which the manifold 122 may be made from a hydrophilic material, the manifold 122 may also wick fluid away from a tissue site while continuing to distribute reduced pressure to the tissue site. The wicking properties of the manifold 122 may draw fluid away from a tissue site by capillary flow or other wicking mechanisms. An example of a hydrophilic foam is a polyvinyl alcohol, open-cell foam such as V.A.C. White-Foam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

A tissue interface may further promote granulation at a tissue site if pressure within a sealed therapeutic environment 124 is reduced. For example, any or all of the surfaces of the manifold 122 may have an uneven, coarse, or jagged profile that can induce microstrains and stresses at a tissue site if reduced pressure is applied through the manifold 122.

In some example embodiments, a tissue interface may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface may further serve as a scaffold for new cell-growth, or a scaffold material may be used in conjunction with the tissue interface to promote cell-growth. In general, a scaffold material may be a biocompatible or biodegradable substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The medical drape 106 is an example of a sealing member. A sealing member may be constructed from a material that can provide a fluid seal between two environments or components, such as between a therapeutic environment and a local external environment. The sealing member may be, for example, an impermeable or semi-permeable, elastomeric film or barrier that can provide a seal adequate to maintain a reduced pressure at a tissue site for a given reduced-pressure source. For semi-permeable materials, the permeability generally should be low enough that a desired reduced pressure may be maintained. An attachment device may be used to attach a sealing member to an attachment surface, such as undamaged epidermis, a gasket, or another sealing member. The attachment device may take many forms. For example, an attachment device may be a medically-acceptable, pressure-sensitive adhesive that extends about a periphery, a portion, or an entire sealing member. Other example embodiments of an attachment device may include a double-sided tape, paste, hydrocolloid, hydrogel, silicone gel, organogel, or an acrylic adhesive.

A "container" broadly includes a canister, pouch, bottle, vial, or other fluid collection apparatus. A container, for example, can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with reduced-pressure therapy.

A reduced-pressure interface 128 may be used to fluidly couple a reduced-pressure delivery conduit 130 to the sealed therapeutic environment 124. The reduced pressure developed by the reduced-pressure source 126 may be delivered through the reduced-pressure delivery conduit 130 to the reduced-pressure interface 128. In one illustrative embodiment, the reduced-pressure interface 128 may be a T.R.A.C.® Pad or Sensa T.R.A.C.® Pad available from KCI of San Antonio, Tex. The reduced-pressure interface 128 allows the reduced pressure to be delivered to the sealed therapeutic environment 124. In other exemplary embodiments, the reduced-pressure interface 128 may also be a conduit inserted through the medical drape 106. The reduced pressure may also be generated by a device directly coupled to the medical drape 106, such as a micropump.

The provision of negative pressure therapy with negative pressure therapy systems, such as the system 100, is increasingly being performed with smaller therapy devices that use battery power rather than a connection to an electrical outlet. Use of battery power decreases the total power supply available to a therapy device. As a result, power drains that would be considered negligible in a device powered through an electrical outlet connection may significantly reduce the ability of the therapy device to provide therapy. A power drain refers to operation of the therapy device that requires use of electrical power, for example, operation of a pump to generate reduced pressure. Power drains may be caused by low-level dressing leaks, for example. A low-level dressing leak can drain power from a battery of a therapy device by repeatedly triggering operation of the therapy device to maintain the necessary reduced pressure at the tissue site. These power drains shorten the useful life of the therapy device before disposal of the therapy device, recharge of the battery, or battery replacement is required. Leak detection techniques may help to identify some leaks that may be then sealed by the user; however, low level leaks will challenge the most sensitive leak detection systems and may often go undetected.

Low level dressing leaks may occur between the medical drape and the epidermis surrounding a tissue site when the medical drape fails to completely seal to the epidermis. Medical drapes are a balance between the strength of the adhesive required to enable the medical drape to seal against leaks and the pain which may result when the medical drape is removed. A bonding adhesive may be better for sealing, but the adhesive strength would cause significantly more discomfort upon medical drape removal. In addition, removing a medical drape with a bonding adhesive may cause significant damage to patients having delicate or damaged skin.

A medical drape that has a sealing adhesive can fill gaps between the drape and the epidermis to limit leaks and can be easy to remove with low discomfort to the patient. Various sealing, gap-filling adhesives, such as silicone, hydrocolloids, and hydrogels, have been tried but each has drawbacks. For example, hydrogel adhesives are usually low tack and prone to swelling, creep, and mobility when used with fluid systems. In another example, silicone adhesives can fill gaps and seal, but are not breathable and may lose the necessary mechanical bonding strength as the silicone adhesives interact with moisture during use. To counter these problems, silicone adhesives often require additional materials to secure the silicone adhesive to the patient. For example, a low leak medical drape may be formed from two adhesive layers: a thick sealing adhesive, perhaps in the shape of a gasket or ring, and a thinner bonding adhesive layer used to keep the sealing adhesive in place. The thinner bonding adhesive may be applied as medical drape strips, or combined with the thicker sealing adhesive as an outer border. Low-leak medical drapes constructed in this way can be more complex than a medical drape using a single adhesive, increasing the complexity of manipulation and operation.

A hybrid medical drape having a thick sealing layer that is perforated and laminated over an adhesive coated film can overcome some of these challenges. For example, a hybrid medical drape may include a film layer having a bonding adhesive applied directly to the film layer, and a sealing adhesive applied directly to the bonding adhesive. The sealing adhesive can be perforated to expose the bonding adhesive. When the medical drape is applied to a patient, the bonding adhesive can be pushed through the perforations of the sealing adhesive to secure the sealing adhesive to the patient. This laminated configuration may provide the benefits of the sealing adhesive and the bonding adhesive over the entire medical drape area. For example, the laminated configuration is able to seal typical low-level leaks, is conformable and of sufficient strength to ensure a seal, and mechanically affixes to the epidermis without secondary processes. The laminated configuration also requires minimal additional application care by the user and can be removable with minimal trauma to the patient.

However, construction of the laminated configuration requires additional assembly steps and an increase in materials that may significantly increase costs. In addition, as two layers of adhesive are applied to the film layer, the total thickness of the medical drape can significantly increase, reducing breathability of the medical drape. Still further, as two full layers of adhesive are applied, significantly more adhesive material is needed to construct the medical drape.

As disclosed herein, the system 100 can overcome these challenges and others by providing a hybrid medical drape with registered adhesives. In some embodiments, for example, the medical drape 106 may have two adhesives, a bonding adhesive and a sealing adhesive, each adhesive coupled to the medical drape 106 with minimal overlap.

Figure 2:
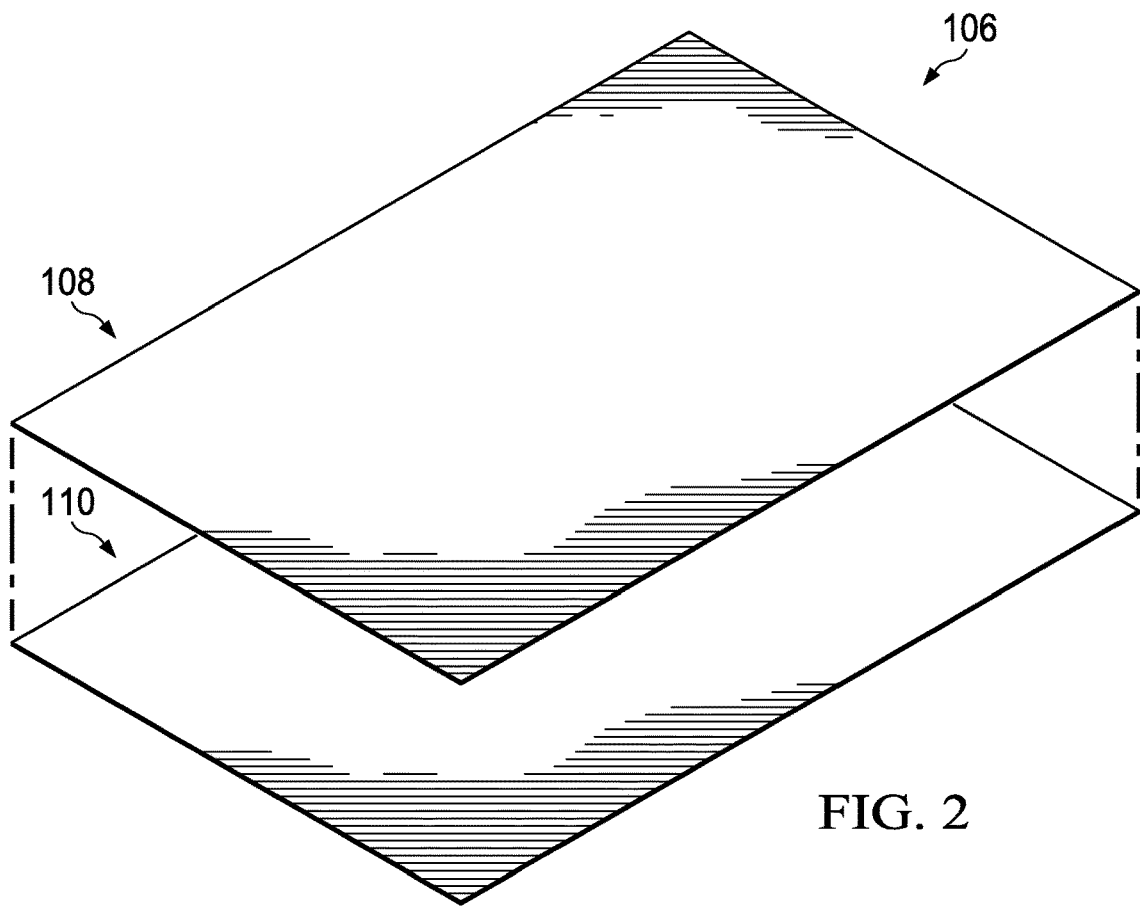
FIG. 2 is an exploded, perspective view of an illustrative embodiment of a medical drape.

FIG. 2 is an exploded perspective view of the medical drape 106 illustrating additional details that may be associated with some embodiments. The medical drape 106 may include a flexible film 108 and an adhesive layer 110 adjacent to the flexible film 108. The flexible film 108 may be a breathable drape, for example, and typically may have a high moisture-vapor-transfer-rate (MVTR). The flexible film 108 may be formed from a range of medically approved films ranging in thickness from about 15 microns (μm) to about 50 microns (μm). The flexible film 108 may comprise a suitable material or materials, such as the following: hydrophilic polyurethane (PU), cellulosics, hydrophilic polyamides, polyvinyl alcohol, polyvinyl pyrrolidone, hydrophilic acrylics, hydrophilic silicone elastomers, and copolymers of these. As one specific, illustrative, non-limiting embodiment, the flexible film 108 may be formed from a breathable cast matt polyurethane film sold by Expopack Advanced Coatings of Wrexham, United Kingdom, under the name INSPIRE 2301.

The high MVTR of the flexible film 108 allows vapor to egress and inhibits liquids from exiting. In some embodiments, the MVTR of the flexible film 108 may be greater than or equal to 300 g/m²/24 hours. In other embodiments, the MVTR of the flexible film 108 may be greater than or equal to 1000 g/m²/24 hours. The illustrative INSPIRE 2301 film may have an MVTR (inverted cup technique) of 14400 g/m²/24 hours and may be approximately 30 microns thick. In other embodiments, a drape having a low MVTR or that allows no vapor transfer might be used. The flexible film 108 can also function as a barrier to liquids and microorganisms.

Figure 3A:
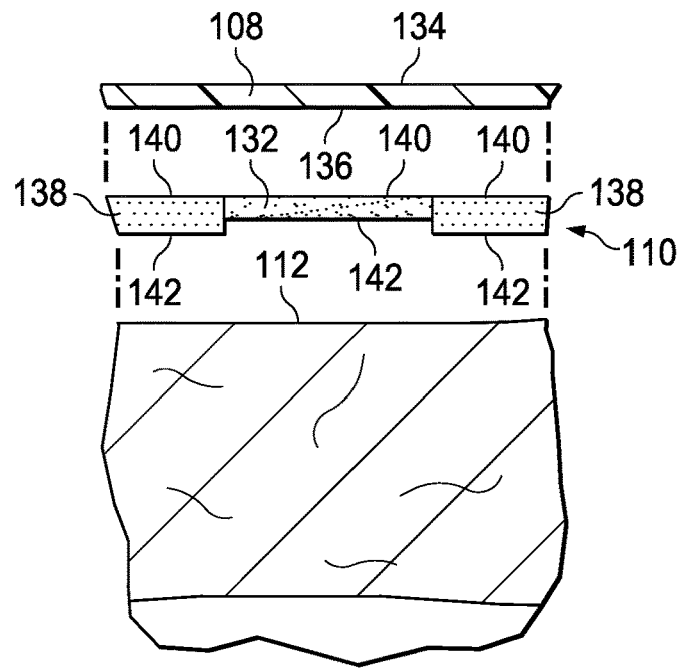
FIG. 3A is an exploded view in cross section of a portion of the system of FIG. 1.

FIG. 3A is an exploded cross sectional view of the medical drape 106 illustrating additional details that may be associated with some embodiments. The flexible film 108 has a first side 134 and a second side 136. The adhesive layer 110 has a first side 140 and a second side 142. The first side 140 of the adhesive layer 110 may be coupled to the second side 136 of the flexible film 108. The adhesive layer 110 may be a medically-acceptable, pressure-sensitive adhesive, glue, bonding agent, or cement, for example. In some embodiments, two adhesives having different characteristics may be used to form the adhesive layer 110. For example, the adhesive layer 110 may include a first adhesive such as a bonding adhesive 132 and a second adhesive such as a sealing adhesive 138. In some embodiments, the placement of the bonding adhesive 132 and the sealing adhesive 138 may be coordinated so that the bonding adhesive 132 and the sealing adhesive 138 both couple to the second side 136 of the flexible film 108.

The bonding adhesive 132 may be a high bond strength acrylic adhesive, patterrubber adhesive, high-tack silicone adhesive, or polyurethane, for example. In some embodiments, the bond strength of the bonding adhesive 132 may have a peel adhesion or resistance to being peeled from a stainless steel material between about 6N/25 mm to about 10N/25 mm on stainless steel substrate at 23° C. at 50% relative humidity based on the American Society for Testing and Materials ("ASTM") standard ASTM D3330. In a non-limiting illustrative example, the bonding adhesive 132 of the adhesive layer 110 comprises an acrylic adhesive with coating weight of 15 grams/m² (gsm) to 70 grams/m² (gsm). The bonding adhesive 132 may be about 30 microns to about 60 microns in thickness.

The sealing adhesive 138 may be an adhesive having a low to medium tackiness, for example, a silicone polymer, polyurethane, or an additional acrylic adhesive. In some embodiments, the bond strength of the sealing adhesive 138 may have a peel adhesion or resistance to being peeled from a stainless steel material between about 0.5N/25 mm to about 1.5N/25 mm on stainless steel substrate at 23° C. at 50% relative humidity based on ASTM D3330. The sealing adhesive 138 may have a tackiness such that the sealing adhesive 138 may achieve the bond strength above after a contact time of less than 60 seconds. Tackiness may be considered a bond strength of an adhesive after a very low contact time between the adhesive and a substrate. In some embodiments, the sealing adhesive 138 may be about 100 microns to about 400 microns thick and have a tackiness that may be about 30% to about 50% of the tackiness of the bonding adhesive 132. The adhesive layer 110 may partially cover the second side 136 of the flexible film 108, leaving portions of the second side 136 of the flexible film 108 free of adhesive.

Figure 3B:
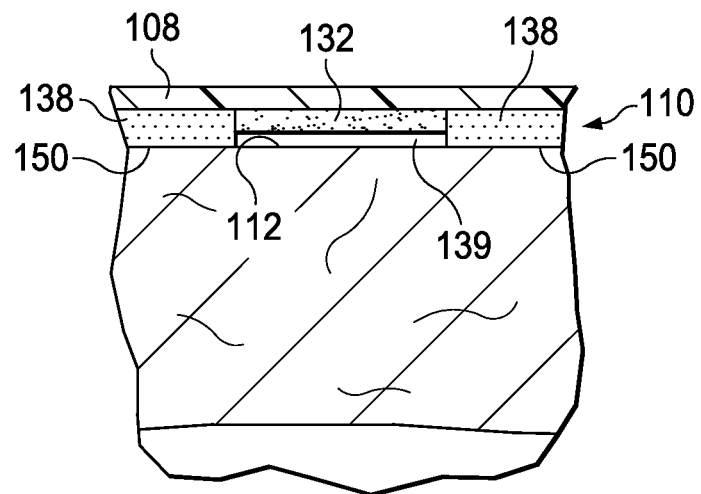
FIG. 3B is an assembled view in cross section of the portion of FIG. 3A with sealing couplings.

FIG. 3B is a sectional view of the medical drape 106 illustrating additional details that may be associated with some embodiments. In some embodiments, the thickness of the bonding adhesive 132 may be less than the thickness of the sealing adhesive 138 so that the adhesive layer 110 may have a varying thickness. If the adhesive layer 110 is placed proximate to or in contact with the epidermis 112 of the patient 104, the second side 142 of the sealing adhesive 138 may be in contact with the epidermis 112 of the patient 104 to form sealing couplings 150. In some embodiments, the thickness of the bonding adhesive 132 may be less than the thickness of the sealing adhesive 138, forming a gap 139 between the bonding adhesive 132 and the epidermis 112.

Figure 3C:
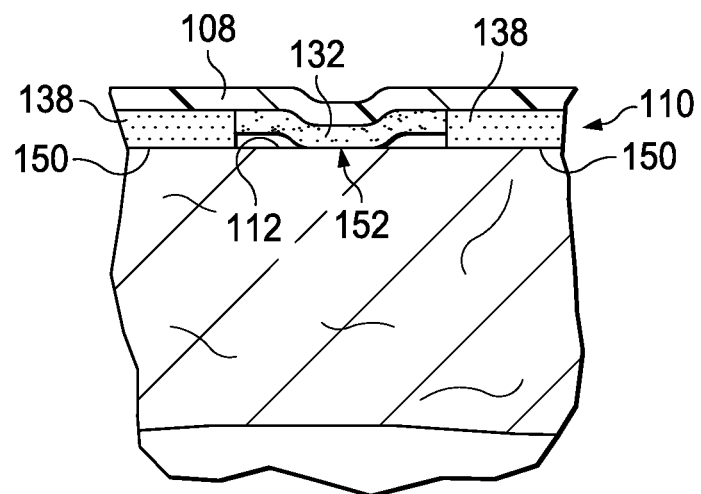
FIG. 3C is an assembled view in cross section of the portion of FIG. 3A with contact couplings.

FIG. 3C is a sectional view of the medical drape 106 illustrating additional details that may be associated with some embodiments. If the medical drape 106 is in a desired location, pressure may be applied to the first side 134 of the flexible film 108. The pressure may cause the second side 142 of the bonding adhesive 132 to be pressed at least partially into contact with the epidermis 112 to form bonding couplings 152. The bonding couplings 152 provide secure, releasable mechanical fixation to the patient 104. The sealing couplings 150 between the sealing adhesive 138 and the epidermis 112 may be sufficient to seal the flexible film 108 to the epidermis 112. The sealing couplings 150 may not be as mechanically strong as the bonding couplings 152 between the bonding adhesive 132 and the epidermis 112.

In operation, according to one illustrative embodiment of the medical drape 106 in the context of the system 100, the manifold 122 may be applied proximate to the tissue site 102. The medical drape 106 may then be disposed over the manifold 122 and the epidermis 112 to form the sealed therapeutic environment 124. In applying the medical drape 106, any release liners may be removed and the second side 142 of the adhesive layer 110 may be applied to the epidermis 112 and over the manifold 122. The tackiness of the sealing adhesive 138 may form sealing couplings 152 and hold the medical drape 106 initially in position. The tackiness of the sealing adhesive 138 may be such that if an adjustment or repositioning is desired, the medical drape 106 may be removed and reapplied or repositioned. If the medical drape 106 is in a desired position, the first side 134 of the flexible film 108 may be pressed, for example, with hand pressure. The pressure causes at least some portion of the bonding adhesive 132 to deform and contact the epidermis 112 to form the bonding couplings 152. The bonding couplings 152 may be a firm—although releasable—attachment. In some embodiments, the bonding couplings 152 may have a peel force against the epidermis 112 between about 0.5N/25 mm to about 2N/25 mm.

The pattern of the bonding adhesive 132 and the pattern of the sealing adhesive 138 may be registered. Registration of the bonding adhesive 132 and the sealing adhesive 138 generally refers to the alignment of the two adhesives relative to one another. In particular, registration of the bonding adhesive 132 and the sealing adhesive 138 may refer to the coordination of adhesive placement on the flexible film 108 to achieve a desired effect. For example, a certain percentage of overlap of one adhesive over the other adhesive, minimal overlap of one adhesive over the other adhesive so that the adhesives are offset from one another, or complete overlap of one adhesive over the other adhesive are all adhesive placements that may be considered registered. For example, the bonding adhesive 132 and the sealing adhesive 138 may be registered by being disposed on the second side 136 of the flexible film 108 so that the bonding adhesive 132 and the sealing adhesive 138 each substantially couple to the second side 136 of the flexible film 108. In addition, the bonding adhesive 132 and the sealing adhesive 138 of the example may be aligned relative to one another to have minimal overlap of one adhesive over the other adhesive. In another example, the sealing adhesive 138 may be offset from the bonding adhesive 132, with both adhesives being coupled to the flexible film 108. Registering the bonding adhesive 132 and the sealing adhesive 138 provides for easier manufacturing and use of the medical drape 106. Registering of the bonding adhesive 132 and the sealing adhesive 138 may also enhance desired properties of the medical drape 106 as described in more detail below. Illustrative, but non-limiting, examples of the registration of the bonding adhesive 132 and the sealing adhesive 138 are described in more detail with respect to the following embodiments.

Figure 4A:
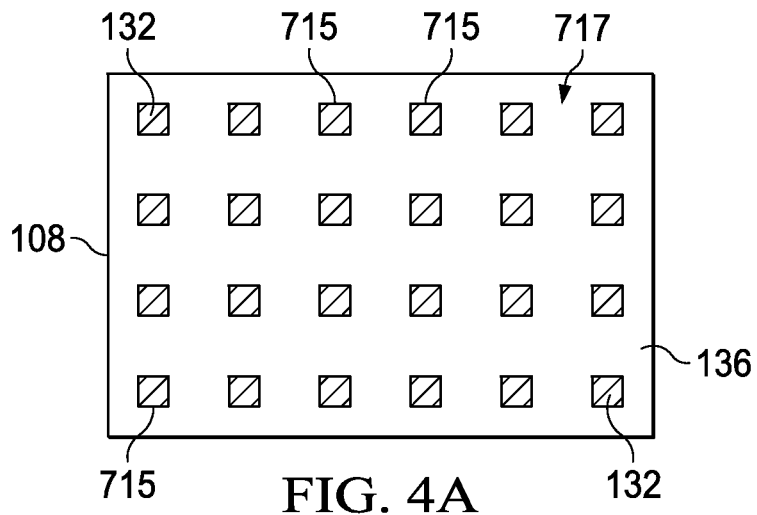
FIG. 4A is a plan view of the medical drape and a portion of an adhesive layer of FIG. 2 having a bonding adhesive disposed thereon.

FIG. 4A is a plan view of the second side 136 of the flexible film 108 illustrating additional details that may be associated with some embodiments. In some embodiments, the bonding adhesive 132 may be formed on or adhered to the flexible film 108 before the sealing adhesive 138. The bonding adhesive 132 may be applied to the second side 136 of the flexible film 108 to form one or more cells 715 of the bonding adhesive 132. In some embodiments, each cell 715 may be separated from adjacent cells 715 so that the cells 715 may generally be equally distributed about the second side 136 of the flexible film 108. The distribution of the cells 715 may leave portions 717 of the second side 136 of the flexible film 108 free of the bonding adhesive 132. The cells 715 may be distributed in a suitable pattern, and the distribution of the cells 715 may depend in part on the intended application of the medical drape 106. Other distributions of the cells 715 are contemplated. In some embodiments, each cell 715 may have a generally square shape, although other shapes, such as rectangular, circular, triangular, amorphous shaped cells, or the like are contemplated. Each cell 715 may have a thickness of about 30 microns to about 60 microns, although other thicknesses may be used.

Figure 4B:
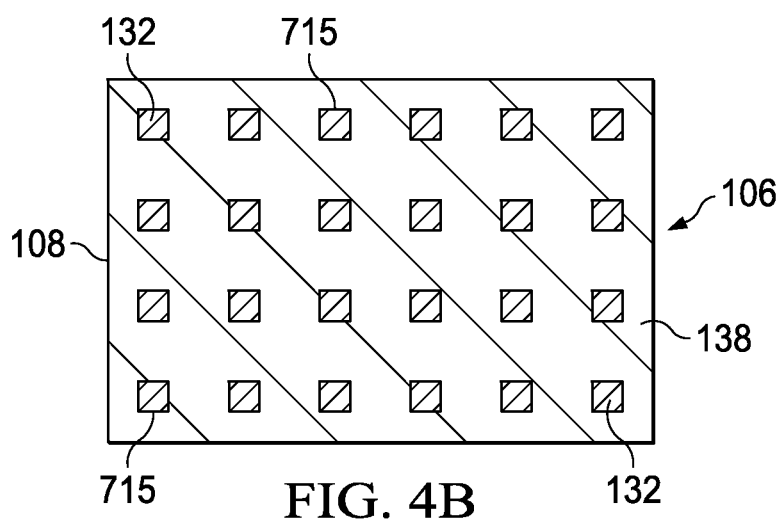
FIG. 4B is a plan view of the medical drape and the adhesive layer of FIG. 2 having the bonding adhesive and a sealing adhesive disposed thereon.

FIG. 4B is a plan view of the second side 136 of the flexible film 108 illustrating additional details that may be associated with some embodiments. In some embodiments, the sealing adhesive 138 may be formed on the flexible film 108 following formation of the cells 715 of the bonding adhesive 132. The sealing adhesive 138 may be distributed so that the portions 717 of the second side 136 of the flexible film 108 between each cell 715 may be covered by the sealing adhesive 138. In some embodiments, distribution of the sealing adhesive 138 on the portions 717 registers the sealing adhesive 138 with the cells 715 of the bonding adhesive 132. In some embodiments, both the sealing adhesive 138 and the bonding adhesive 132 may be applied substantially to the second side 136 of the flexible film 108 with minimal overlap of the sealing adhesive 138 and the bonding adhesive 132. In other embodiments, the sealing adhesive 138 may be disposed on the second side 136 of the flexible film 108 prior to placement of the bonding adhesive 132 on the second side 136 of the flexible film 108. Some overlap between the bonding adhesive 132 and the sealing adhesive 138 may occur during manufacturing. The sealing adhesive 138 may have a thickness of about 100 microns to about 400 microns, although other thicknesses may be used. In some embodiments, the bonding adhesive 132 and the sealing adhesive 138 collectively cover substantially all of the second side 136 of the flexible film 108. In other embodiments, the bonding adhesive 132 and the sealing adhesive 138 may collectively cover a portion of the second side 136 of the flexible film 108 that may be less than the entirety of the second side 136.

Figure 5A:
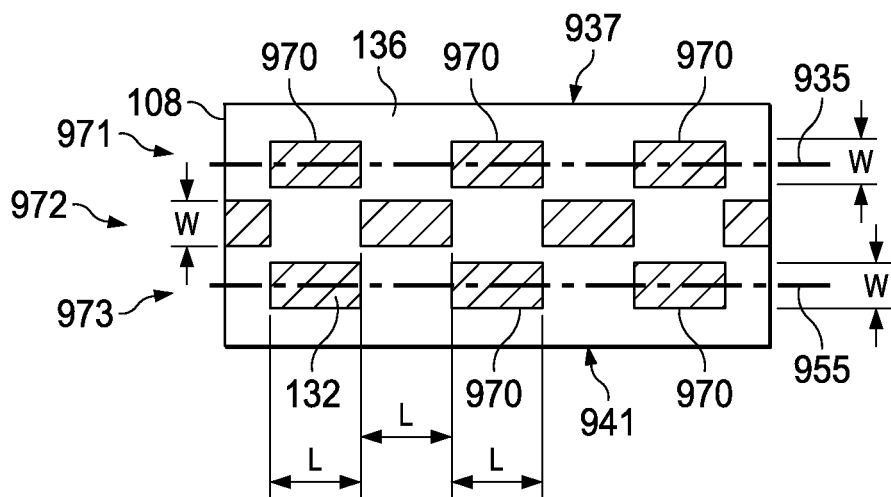
FIG. 5A is a plan view of the medical drape and a portion of the adhesive layer of FIG. 2 having a bonding adhesive disposed thereon.

FIG. 5A is a plan views of the medical drape 106 illustrating additional details that may be associated with some embodiments. In some embodiments, the bonding adhesive 132 may first be deposited on the second side 136 of the flexible film 108. The bonding adhesive 132 may be distributed on the second side 136 of the flexible film 108 so that the bonding adhesive 132 forms a checkerboard pattern having cells 970 of the bonding adhesive 132 that may be offset from the cells 970 on adjacent rows. As shown, the cells 970 of the bonding adhesive 132 in this example embodiment may be disposed on the second side 136 of the flexible film 108 in three rows 971, 972, and 973. More or fewer rows may be used. In some embodiments, the cells 970 may be rectangular. In other embodiments, the cells 970 may be other shapes including, rectangular, square, circular, ovoid, triangular, amorphously shaped, or the like. Each cell 970 of each row may have a first dimension having a first orientation with respect to a first edge 937 of the flexible film 108 and a second dimension having a second orientation with respect to the first edge 937 of the flexible film 108. In some embodiments, each cell 970 may be rectangular in shape. The first dimension may be a length L, and the second dimension may be a width W. In some embodiments, the length L may be approximately twice the width W of each cell 970. In other embodiments, the cells 970 of each row may be differently shaped from the cells 970 of prior and successive rows.

In some embodiments, the length L of the cells 970 of the first row 971 may be aligned with a first edge 937 of the flexible film 108. The first row 971 may also be aligned with a second edge 941 of the flexible film 108 that may be opposite the first edge 937. In some embodiments, the cells 970 of the first row 971 may be disposed proximate to the first edge 937 of the flexible film 108. Each cell 970 of the first row 971 may be separated from adjacent cells 970 of the first row 971. The separation of adjacent cells 970 may provide a portion of the second side 136 of the flexible film 108 between each cell 970 that is free of the bonding adhesive 132. In some embodiments, the separation between each cell 970 of the first row 971 may be about the length L. A reference line 935 of the first row 971 may be aligned with a center of the width W of the cells 970 of the first row 971.

The second row 972 may be disposed adjacent to the first row 971 along the width of the flexible film 108. The second row 972 may be offset from the cells 970 of the first row 971 along the length of the flexible film 108. In some embodiments, the cells 970 of the second row 972 align with separation between the cells 970 of the first row 971, that is, between the cells 970 of the first row 971. In the illustrative embodiment of FIG. 5A, a corner of a cell 970 of the first row 971 proximate to the second edge 941 is proximate to a corner of a cell 970 of the second row 972 that is proximate to the first edge 937. Each cell 970 of the second row 972 may be separated from adjacent cells 970 of the second row 972. In some embodiments, a portion of the second side 136 of the flexible film 108 may be substantially free of the bonding adhesive 132 between each cell 970 of the second row 972. In some embodiments, the separation between the cells 970 of the second row 972 may be about the length L of each cell 970.

The third row 973 may be disposed adjacent to the cells 970 of the second row 972 along the width of the flexible film 108. The cells 970 of the third row 973 may be offset from the cells 970 of the second row 972 and aligned with the cells 970 of the first row 971 along the length of the flexible film 108. As shown in the illustrative embodiment of FIG. 5A, a corner of a cell 970 of the second row 972 proximate to the second edge 941 may be proximate to a corner of a cell 970 of the third row 973 that is proximate to the first edge 937. Each cell 970 of the third row 973 may be separated from adjacent cells 970 of the third row 973. In some embodiments, a portion of the second side 136 of the flexible film 108 may be free of the bonding adhesive 132 between each cell 970 of the third row 973. In some embodiments, the separation between each cell 970 of the third row 973 may be approximately equal to the length L of each cell 970 of the third row 973. The third row 973 may have a reference line 955 aligned with a center of the width W of the cells 970 of the third row 973. In some embodiments, the rows 971-973 may be evenly distributed across the width of the flexible film 108 between the first edge 937 and the second edge 941.

Figure 5B:
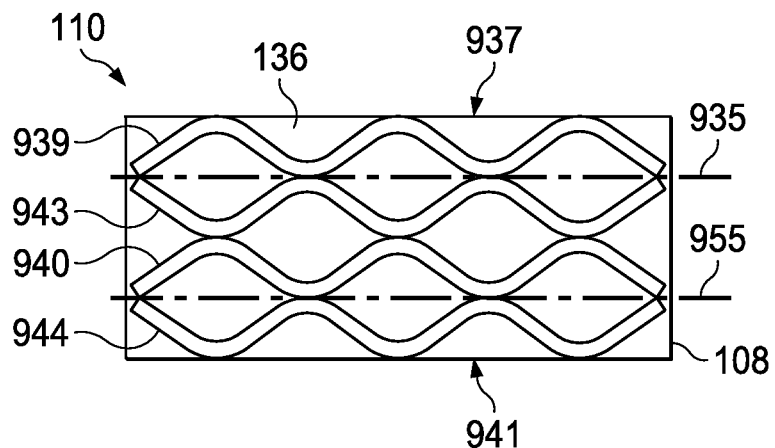
FIG. 5B is a plan view of the medical drape and a portion of the adhesive layer of FIG. 2 having a sealing adhesive disposed thereon.

FIG. 5B is a plan view of the second side 136 of the flexible film 108 illustrating additional details that may be associated with some embodiments. In some embodiments, the sealing adhesive 138 may be disposed on the second side 136 of the flexible film 108 in strips. In some embodiments, there may be four strips of the sealing adhesive 138: a first strip 939, a second strip 943, a third strip 940, and a fourth strip 944. In some embodiments, each strip may have an oscillating shape, such as the illustrated sinusoidal wave or other periodically oscillating wave shape. In some embodiments, each strip may propagate parallel to the first edge 937 and the second edge 941. The first strip 939 and the second strip 943 may be oriented with the respect to the reference line 935. The maximum and minimum amplitudes of the first strip 939 and the second strip 943 may be determined relative to the reference line 935. The third strip 940 and the fourth strip 944 may be oriented with respect to the reference line 955. The maximum and minimum amplitudes of the third strip 940 and the fourth strip 944 may be determined relative to the reference line 955.

Figure 5C:
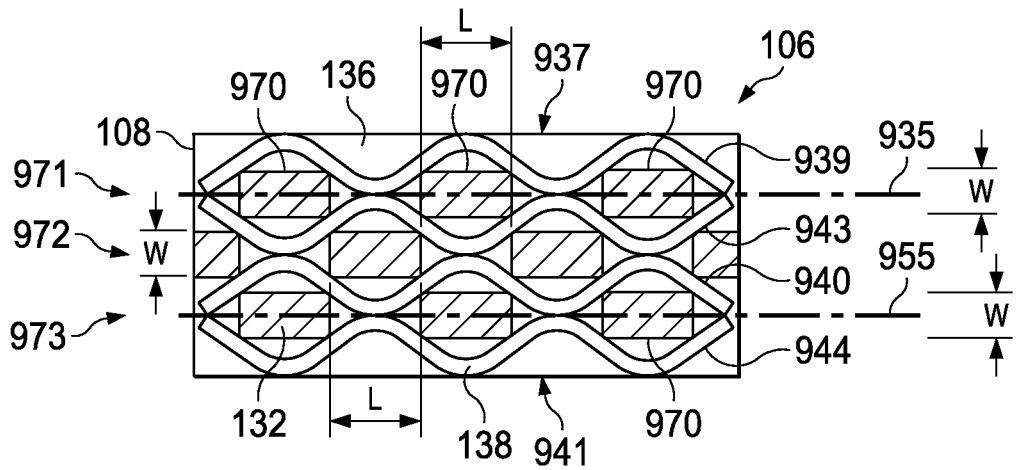
FIG. 5C is a plan view of the medical drape and the adhesive layer of FIG. 2 having the bonding adhesive of FIG. 5A and the sealing adhesive of FIG. 5B disposed thereon.

FIG. 5C is a plan view of the second side 136 of the flexible film 108 illustrating additional details that may be associated with some embodiments. In some embodiments, a maximum amplitude of the first strip 939 and the second strip 943 may align with a center of the length L of the cells 970 of the first row 971. The first strip 939 and the second strip 943 may have a minimum amplitude proximate to reference line 935. The first strip 939 and the second strip 943 may have a frequency so that the minimum amplitude may align with a center of the length L of the cells 970 of the second row 972. In some embodiments, each of the first strip 939 and the second strip 943 may have an amplitude approximately equivalent to the width W of the cells 970 of the first row 971. In some embodiments, the first strip 939 and the second strip 943 of the sealing adhesive 138 may substantially enclose the cells 970 of the bonding adhesive 132 in the first row 971. Similarly, due to the offset of the cells 970 of the second row 972 from the cells 970 of the first row 971, the second strip 943 may also partially enclose the second row 972 of the bonding adhesive 132.

The third strip 940 and the fourth strip 944 of the sealing adhesive 138 may be deposited similarly. For example, the third strip 940 and the fourth strip 944 of the sealing adhesive 138 may be deposited proximate to the third row 973 of the bonding adhesive 132. In some embodiments, the third strip 940 and the fourth strip 944 may have a maximum amplitude from the reference line 955. The maximum amplitude of the third strip 940 and the fourth strip 944 may align with a center of the length L of the cells 970 of the third row 973. The third strip 940 and the fourth strip 944 may have a minimum amplitude proximate to reference line 955. The third strip 940 and the fourth strip 944 may have a frequency so that the minimum amplitude may align with a center of the length L of the cells 970 of the second row 972. In some embodiments, the third strip 940 and the fourth strip 944 may have an amplitude approximately equivalent to the width W of the cells 970 of the third row 973. In some embodiments, the third strip 940 and the fourth strip 944 of the sealing adhesive 138 may enclose the cells 970 of the bonding adhesive 132 in the third row 973. Due to the offset of the cells 970 of the third row 973 with the cells 970 of the second row 972, the third strip 940 may partially enclose the second row 972 of the bonding adhesive 132.

The bonding adhesive 132 and the sealing adhesive 138 may cover only a portion of the second side 136 of the flexible film 108. In some embodiments, each cell 970 of the bonding adhesive 132 may be at least partially enclosed by the sealing adhesive 138. In some embodiments, the sealing adhesive 138 may be disposed on the second side 136 of the flexible film 108 prior to the disposition of the bonding adhesive 132 on the second side 136 of the flexible film 108. In some embodiments, the bonding adhesive 132 and the sealing adhesive 138 are registered. For example, portions of the second side 136 of the flexible film 108 covered by the bonding adhesive 132 may be different than the portions of the second side 136 of the flexible film 108 covered by the sealing adhesive 138. However, some overlap between the bonding adhesive 132 and the sealing adhesive 138 may occur.

Figure 6A:
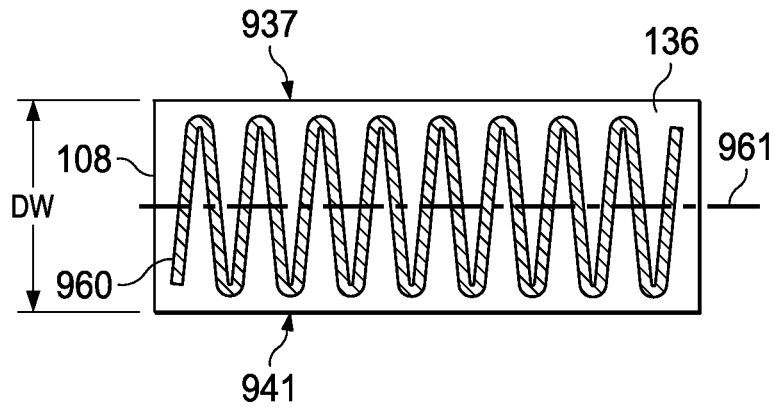
FIG. 6A is a plan view of the medical drape and a portion of the adhesive layer of FIG. 2 having a bonding adhesive disposed thereon.
Figure 6B:
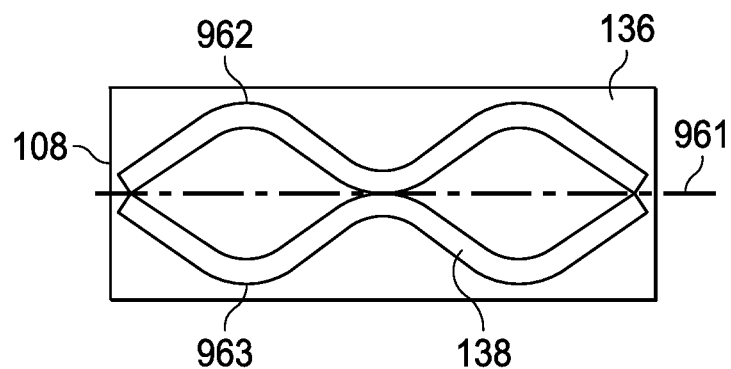
FIG. 6B is a plan view of the medical drape and a portion of the adhesive layer of FIG. 2 having a sealing adhesive disposed thereon.
Figure 6C:
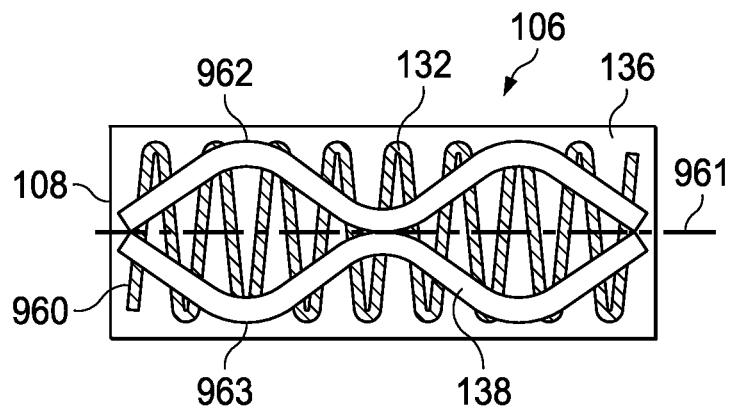
FIG. 6C is a plan view of the medical drape and the adhesive layer of FIG. 2 having the bonding adhesive of FIG. 6A and the sealing adhesive of FIG. 6B disposed thereon.

FIGS. 6A-6C are plan views of the second side 136 of the flexible film 108 illustrating the bonding adhesive 132 and the sealing adhesive 138 disposed in another pattern that may be associated with other embodiments. In some embodiments, the bonding adhesive 132 may first be deposited on the second side 136 of the flexible film 108 as shown in FIG. 6A. The flexible film 108 may have a reference line 961 aligned with a center of the width DW of the flexible film 108. The reference line 961 may be generally parallel to the first edge 937 and the second edge 941 of the flexible film 108. The bonding adhesive 132 may be deposited as a strip 960 of adhesive having an oscillating wave shape. For example, the strip 960 may have a sinusoidal wave shape, square-wave shape, or other periodically oscillating shape. In some embodiments, the strip 960 may have a peak-to-peak amplitude across the reference line 961 approximately equivalent to the width DW of the flexible film 108. The amplitude of the strip 960 may be other amplitudes so that the flexible film 108 may have multiple strips 960. For example, in other embodiments, the strip 960 may comprise two strips having a peak-to-peak amplitude equivalent to one-half the width of the flexible film 108, and the strips 960 may not cross the reference line 961.

A first strip 962 and a second strip 963 of sealing adhesive 138 having an oscillating wave shape may be deposited on the second side 136 of the flexible film 108. The oscillating wave shape of the first strip 962 and the second strip 963 may have a sine-wave shape, square-wave shape, or other periodically oscillating shape, for example. The first strip 962 and the second strip 963 may be disposed on opposite sides of the reference line 961 and propagate parallel to the first side 937 and the second side 941 of the flexible film 108. In some embodiments, the strip 960 may have a frequency greater than the frequency of the first strip 962 and the second strip 963 so that, for a given length of the flexible film 108, the bonding adhesive 132 of the strip 960 may provide more coverage of the second side 136 than the sealing adhesive 138 of the first strip 962 and the second strip 963. The amplitudes and the frequencies of the strip 960, the first strip 962, and the second strip 963 may vary as needed depending on the application of the particular medical drape 106.

As illustrated in FIG. 5A-6C, there may be portions of the second side 136 of the flexible film 108 free of adhesives. Portions of the flexible film 108 that may be free of adhesive may expose more of the flexible film 108 directly to moisture. Increasing the direct exposure of the flexible film 108 to moisture may enhance vapor transmission, for example. Increasing vapor transmission may provide a corresponding increase in MVTR.

There may be a number of ways that the medical drape 106 may be manufactured. For example, a method of manufacturing a medical drape may include disposing a first adhesive on a side of the flexible film in a first pattern and disposing a second adhesive on the side of the flexible film in a second pattern so that the first adhesive and the second adhesive cover substantially different portions of the flexible film. The first pattern and the second pattern may be deposited by moving the flexible film past a rotary member so that the flexible film contacts a portion of an exterior of the rotary member while the flexible film moves relative to the rotary member. The rotary member may have openings formed in the exterior surface of the rotary member or an engraved portion in at least one of the first pattern and the second pattern. In some embodiments, one of the adhesives may be supplied to an interior of the rotary member, and the adhesive may be compressed through openings of the rotary member onto the flexible film. In other embodiments, one of the adhesives may be coated into the engraving on the exterior portion of the rotary member, and the adhesive may be transferred from the rotary member onto the flexible film. In still another embodiment, the adhesives may be deposited by extruding the adhesives onto the flexible film.

FIG. 7A is a schematic diagram illustrating an example embodiment of an apparatus 700 for manufacturing the medical drape 106. The flexible film 108 may be provided on a conveyor assembly 701. The conveyor assembly 701 may be, for example, a belt conveyor, gravity conveyor, bucket conveyor, roller conveyor, chain conveyor, vibrating conveyor, or other suitable device, configured to transport the flexible film 108 through the apparatus 700. The conveyor assembly 701 may be one or more conveyor systems or a single conveyor system as schematically illustrated in FIG. 7A. The conveyor assembly 701 may include additional components not illustrated or described herein that can support and operate the described components. The conveyor assembly 701 may include one or more rollers 705. The rollers 705 may be configured to cause translation of a belt or carrier, such as belt 703, and may be free-spinning or motorized. The flexible film 108 may be provided to the conveyor assembly 701. In some embodiments, the flexible film 108 may be provided to the conveyor assembly 701 in sheets that may appear continuous to the conveyor assembly 701. For example, the flexible film 108 may be provided in rolls that may be disposed onto the conveyor assembly 701. The conveyor assembly 701 may unroll the roll of the flexible film 108 as the conveyor assembly 701 moves a first end of the flexible film 108 through the process. The flexible film 108 may be disposed on the conveyor assembly 701 so that the second side 136 of the flexible film 108 may face away from the belt 703 of the conveyor assembly 701. In some embodiments, the flexible film 108 may move in response to movement of the belt 703 of the conveyor assembly 701.

Figure 7B:
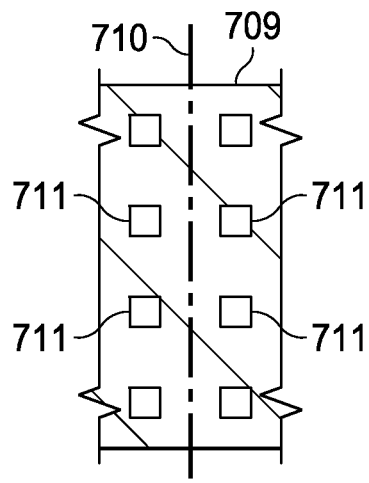
FIG. 7B is a schematic diagram of a portion of an exterior surface of a first rotary screen of FIG. 7A.

As shown in FIG. 7A, the conveyor assembly 701 may convey the flexible film 108 to a first screen assembly, such as screen assembly 707. The screen assembly 707 may include additional components not illustrated herein that support and operate the components described below. The screen assembly 707 may include a first rotary screen, such as rotary screen 709. The rotary screen 709 may be a cylinder having a polymeric or metal material mounted on an exterior portion of the cylinder so that the material forms a side surface of the rotary screen 709. The rotary screen 709 may have one or more openings 711 extending through the material of the rotary screen 709 to form a screen or mesh that allows an adhesive or other bonding material to flow through the rotary screen 709. The openings 711 may form a pattern so that the flow may be passively controlled. In some embodiments, the openings 711 may form a mesh having portions blocked to prevent flow at those locations. In one illustrative embodiment, the openings 711 in the rotary screen 709 correspond with a desired distribution of the bonding adhesive 132. FIG. 7B illustrates a portion of an exterior surface of the rotary screen 709. In some embodiments, the openings 711 may be one or more openings spaced axially parallel to an axis 710 of the rotary screen 709 and spaced around the circumference of the rotary screen 709. In a non-limiting illustrative embodiment, the openings 711 may be square shaped. An adhesive may be transferred through the square shape of the openings 711 to the flexible film 108, forming the one or more cells 715 distributed on the second side 136 of the flexible film 108 as illustrated in FIGS. 4A and 4B, for example.

Referring again to FIG. 7A, the rotary screen assembly 707 may also include a first press, such as press 719. The press 719 may be disposed within an interior surface 721 of the rotary screen 709. The press 719 may be configured to compress a bonding material, such as the bonding adhesive 132, against the interior surface 721 of the rotary screen 709 and through the openings 711. In some embodiments, the press 719 may be a weighted object configured to roll along a bottom of the rotary screen 709. The press 719 may be a cylindrical weight positioned so that the side surface of the press 719 may be in contact with the interior surface 721. As the rotary screen 709 rotates, the press 719 may rotate and remain in contact with the interior surface 721. For example, the press 719 may be formed of a material having sufficient weight to remain in contact with the interior surface 721 during rotation or operation of the rotary screen 709. In other illustrative embodiments, the press 719 may be fixed on an axle to prevent relative linear motion between the rotary screen 709 and the press 719. The axle may be fixed or may float and be biased to maintain the press 719 in contact with the interior surface 721. In other embodiments, the press 719 may be motorized. In still other embodiments, the press 719 may be a blade or squeegee that does not rotate.

A bonding adhesive 720 may be supplied to the interior surface 721 of the rotary screen 709 by a suitable means, provided that the bonding adhesive 720 may be suitably viscous to flow through the rotary screen 709. In some embodiments, for example, the viscosity range of the bonding adhesive 132 may be between about 100 mPa·s to 10000 mPa·s. The bonding adhesive 132 may be pseudoplastic, that is, the viscosity of the bonding adhesive 132 may be proportional to the applied shear rate and shear thinning so that, at relatively high shear, the bonding adhesive 132 has a low viscosity. As the rotary screen 709 rotates in the direction indicated by the arrow 723 and the conveyor assembly 701 moves the flexible film 108 in the direction indicated by the arrow 725, the flexible film 108 may pass between the conveyor assembly 701 and a contact patch 727 of the rotary screen 709. The contact patch 727 may be that portion of the rotary screen 709 in contact with or adjacent to the belt 703 of the conveyor assembly 701 at a given moment during the manufacturing process. The press 719 may be disposed within the interior surface 721 of the rotary screen 709 adjacent to the contact patch 727.

As the rotary screen 709 rotates, the bonding adhesive 720 may be carried toward the press 719. Continued rotation of the rotary screen 709 causes the bonding adhesive 720 to engage the press 719, and the press 719 forces the bonding adhesive 720 through the openings 711 and onto the second side 136 of the flexible film 108. The press 719 remains adjacent to the contact patch 727 during operation of the screen assembly 707. The speed of rotation of the rotary screen 709 and the linear speed of the flexible film 108 through the conveyor assembly 701 may determine the amount and thickness of the bonding adhesive 720 deposited onto the second side 136 of the flexible film 108 as the cells 715 of the bonding adhesive 132. In some embodiments, the speed of the flexible film 108 through the conveyor assembly 701 and the speed of the rotary screen 709 may also be coordinated to control the distance between each cell 715 that may be deposited on the flexible film 108.

The conveyor assembly 701 may continue to move the flexible film 108 following passage of the flexible film 108 through the screen assembly 707. The conveyor assembly 701 may move the flexible film 108 and the cells 715 of the bonding adhesive 132 past a curing or drying assembly, such as curing assembly 729. The curing assembly 729 may be a suitable apparatus configured to cure or dry the cells 715 of the bonding adhesive 132 while the conveyor assembly 701 moves the flexible film 108 past the curing assembly 729. Other exemplary embodiments may not include the curing assembly 729. Following transfer of the bonding adhesive 132, the bonding adhesive 138 may increase in viscosity, through drying or curing whether assisted or unassisted, so that the bonding adhesive 132 may resist flow under the application conditions for the medical drape 106.

The conveyor assembly 701 may convey the flexible film 108 to a second screen assembly, such as screen assembly 731. The screen assembly 731 may include additional components not illustrated herein that support and operate the components described below. The screen assembly 731 may include a second rotary screen, such as rotary screen 733. The rotary screen 733 may be a cylinder having a polymeric or metal material mounted on an exterior portion of the cylinder so that the material forms a side surface of the rotary screen 733. The rotary screen 733 may have one or more openings 735 extending through the material of the rotary screen 733 to form a screen that allows an adhesive or other bonding material to flow through the rotary screen 733. The openings 735 may form a pattern that permits flow through the rotary screen 733 to be passively controlled. In some embodiments, the openings 735 in the rotary screen 733 correspond with a desired distribution of the sealing adhesive 138. The openings 735 may be one or more openings axially separated along a length of the rotary screen 733 parallel to an axis 738 of the rotary screen 733 and separated around the circumference of the rotary screen 733. In other embodiments, the openings 735 may be a mesh permitting flow of a bonding material, through a substantial portion of the side surface of the rotary screen 733.

Figure 7C:
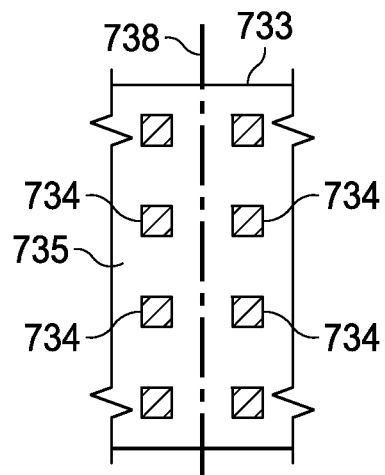
FIG. 7C is a schematic diagram of a portion of an exterior surface of a second rotary screen of FIG. 7A.

FIG. 7C illustrates a portion of the exterior surface of the rotary screen 733. In some embodiments, the openings 735 may constitute a large portion of the exterior surface of the rotary screen 733. Barriers 734 may be disposed on the mesh forming the outer surface of the rotary screen 733. The barriers 734 may be disposed at certain locations around the circumference of the rotary screen 733, blocking communication through the side surface of the rotary screen 733. In some embodiments, the barriers 734 may be separated and axially parallel to an axis 738 of the rotary screen 733. The barriers 734 may also be separated around the circumference of the rotary screen 733. In some embodiments, the orientation of the barriers 734 on the side surface of the rotary screen 733 aligns the barriers 734 with the cells 715 of the bonding adhesive 132 previously applied to the second side 136 of the flexible film 108 by the first screen apparatus 707. The configuration of the barriers 734 permits application of the sealing adhesive 138 to the portions 717 of the second side 136 of the flexible film 108, but not to the cells 715 of the bonding adhesive 132 on the second side 136 of the flexible film 108 as shown in FIG. 4B.

The screen assembly 731 may also include a second press, such as a press 739. The press 739 may be disposed within an interior of the rotary screen 733 and configured to compress an adhesive or bonding material, such as the sealing adhesive 138, against an interior surface 741 of the rotary screen 733. In some embodiments, the press 739 may be a weighted object configured to roll along a bottom of the rotary screen 733. In one non-limiting example, the press 739 may be a cylindrical weight positioned so that a side surface of the press 739 may be in contact with the interior surface 741. As the rotary screen 733 rotates, the press 739 may rotate and remain in contact with the interior surface 741. The press 739 may be formed of a suitable material having sufficient weight to remain in contact with the interior surface 741 during rotation or operation of the rotary screen 733. In other exemplary embodiments, the press 739 may be fixed on an axle to prevent relative linear motion between the rotary screen 733 and the press 739. The axle may be fixed or may float and be biased to maintain the press 739 in contact with the interior surface 741. In other embodiments, the press 739 may be motorized. In still other embodiments, the press 739 may not rotate.

A sealing adhesive 740 may be supplied to the interior of the rotary screen 733 by a suitable means, provided that the sealing adhesive 740 has a suitable viscosity to allow flow of the sealing adhesive 740 through the openings 735. In some embodiments, for example, the viscosity range of the sealing adhesive 138 may be between about 100 mPa·s to 10000 mPa·s. The sealing adhesive 138 may be pseudoplastic, that is, the viscosity of the sealing adhesive 138 may be proportional to the applied shear rate and shear thinning so that, at relatively high shear, the sealing adhesive 138 has a low viscosity. As the rotary screen 733 rotates in the direction indicated by the arrow 743 and the conveyor assembly 701 moves in the direction indicated by the arrow 725, the flexible film 108 may pass between the conveyor assembly 701 and a contact patch 745 of the rotary screen 733. The contact patch 745 may be that portion of the rotary screen 733 in contact with or adjacent to the upper surface 703 of the conveyor assembly 701 at a given moment during the manufacturing process. The press 739 may be disposed within the interior 741 of the rotary screen 733 adjacent to the contact patch 745. As the rotary screen 733 rotates, the sealing adhesive 740 may be carried toward the press 739. As the sealing adhesive 740 engages the press 739, the press 739 may force the sealing adhesive 740 through the openings 735 and onto the second side 136 of the flexible film 108 as the sealing adhesive 138. The press 739 may remain adjacent to the contact patch 745 during operation of the screen assembly 731. If the openings 735 are a mesh having portions blocked to prevent flow, the sealing adhesive 740 may be deposited as the sealing adhesive 138. As shown in FIG. 4B, the sealing adhesive 138 may register with the cells 715 to cover the portions 717 of the second side 136 of the flexible film 108, leaving the cells 715 of the bonding adhesive 132 exposed.

Continuing to refer to FIG. 7A, the speed of rotation of the rotary screen 733 and the linear speed of the conveyor assembly 701 may be configured to control the amount of the sealing adhesive 720 deposited or transferred onto the second side 136 of the flexible film 108. In some embodiments, the speed of the conveyor assembly 701 and the speed of the rotary screen 739 may be coordinated so that the sealing adhesive 740 may be deposited between each cell 715 of the bonding adhesive to cover the portions 717.

The conveyor assembly 701 may continue to move the flexible film 108 following passage of the flexible film 108 through the screen assembly 731. The conveyor assembly 701 may move the flexible film 108 having the adhesive layer 110, formed of the bonding adhesive 132 and the sealing adhesive 138 disposed thereon, past a curing assembly, such as curing assembly 747. The curing assembly 747 may be a suitable apparatus configured to cure the sealing adhesive 138 while the conveyor assembly 701 moves the flexible film 108 past the curing assembly 747. Other exemplary embodiments do not include the curing assembly 747. Following transfer of the sealing adhesive 138, the sealing adhesive 138 may increase in viscosity, through drying or curing whether assisted or unassisted, so that the sealing adhesive 138 may resist flow under the application conditions for the medical drape 106. The rotary screen 709 and the rotary screen 733 may have a suitable formation of openings 711, 735 to apply a desired adhesive pattern on the second side 136 of the flexible film 108.

Figure 8B:
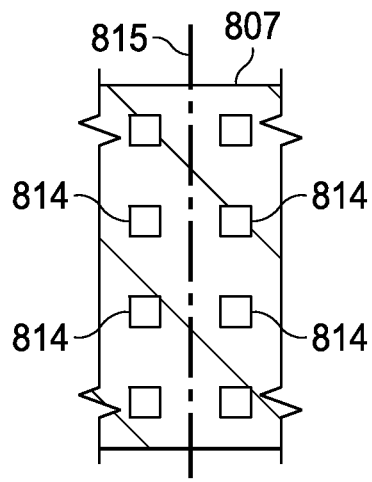
FIG. 8B is a schematic diagram of a portion of an exterior surface of a first transfer cylinder of FIG. 8A.

FIGS. 8A-8E are schematic diagrams illustrating another example apparatus 800 for manufacturing some embodiments of the medical drape 106. The flexible film 108 may be provided on a conveyor assembly 801. The conveyor assembly 801 may include one or more rollers 803 through which the flexible film 108 may be conveyed. Generally, the rollers 803 may suspend the flexible film 108 and may be motorized or otherwise powered so that the flexible film 108 may be carried through the conveyor assembly 801. The conveyor assembly 801 may be one or more conveyor systems or a single conveyor system as schematically illustrated in FIG. 8A. The flexible film 108 may be provided to the conveyor assembly 801 in a suitable manner. In some embodiments, the flexible film 108 may be provided to the conveyor assembly 801 so that the conveyor assembly 801 receives the flexible film 108 in a continuous or nearly continuous sheet during operation of the conveyor assembly 801. For example, the flexible film 108 may be provided in rolls that may be disposed onto the conveyor assembly 801. The conveyor assembly 801 may unroll the rolls of the flexible film 108 as the conveyor assembly 801 moves a first end of the flexible film 108 through the apparatus 800.

The conveyor assembly 801 may convey the flexible film 108 to a first transfer assembly, such as a transfer assembly 805. The transfer assembly 805 may include additional components not illustrated herein to support and operate the schematically illustrated components. The transfer assembly 805 may include a first transfer cylinder, such as a transfer cylinder 807, a first well, such as a well 809, a first impression roll, such as an impression roll 811, and a first blade, such as a blade 813, for example. The transfer cylinder 807 may be a cylinder having a side surface with an engraved pattern 814 formed in an exterior of the side surface of the cylinder. The well 809 may be a suitable container having an interior configured to house or store an adhesive or bonding material, such as the bonding adhesive 132. In some embodiments, the adhesive or bonding material may be stored in a liquid form. In other embodiments, the adhesive or bonding material may be stored in a gel form. In the illustrative embodiments, the bonding adhesive 132 may be housed in the well 809 in a suitably viscous form. The viscosity range of the bonding adhesive 132 may be between about 100 mPa·s to 10000 mPa·s. The bonding adhesive 132 may be pseudoplastic, that is, the viscosity of the bonding adhesive 132 may be proportional to the applied shear rate and shear thinning so that, at relatively high shear, the bonding adhesive 132 has a low viscosity. The transfer cylinder 807 and the well 809 may be disposed adjacent to each other so that a portion of the transfer cylinder 807 may be submerged in the bonding adhesive 132 during operation of the transfer assembly 805, submerging at least a portion of the engraved pattern 814 of the transfer cylinder 807 in the bonding adhesive 132.

In some embodiments, the well 809 may be mounted to a floor or other suitable support device and have an upper portion opposite the floor that may be open to the ambient environment. The transfer cylinder 807 may be mounted on an axle 815 so that a lower portion of the transfer cylinder 807 may be disposed within the interior of the well 809. The transfer cylinder 807 may be rotatable about an axle 815 passing through a center of the transfer cylinder 807. In some embodiments, the transfer cylinder 807 rotates about the axle 815 in the direction indicated by the arrow 817. As the transfer cylinder 807 rotates about the axle 815, the lower portion may be submerged in the bonding adhesive 132 housed within the well 809. While submerged, the bonding adhesive 132 may be drawn into the engraved pattern 814, filling the engraved pattern 814 with the bonding adhesive 132. In an embodiment, the bonding adhesive 132 may be drawn into the engraved pattern 814 by capillary action caused by the inter-molecular attractive forces between the bonding adhesive 132 and the engraved pattern 814. For example, adhesion forces between the bonding adhesive 132 and the solid surface of the engraved pattern 814 may pull the bonding adhesive 132 into the engraved pattern 814. As the submerged portion rotates out of the well 809, the submerged portion of the transfer cylinder 807 may rotate past the blade 813. The blade 813 may be a squeegee configured to exert a force on the surface of the transfer cylinder 807 and may be formed of a rubber based material or the like. The blade 813 may be in contact with the exterior surface of the transfer cylinder 807 so that, as the transfer cylinder 807 rotates out of the well 809, excess amounts of the bonding adhesive 132, which may not be located in the engraved pattern 814, may be scraped or removed from the exterior surface of the transfer cylinder 807.

Continued rotation of the transfer cylinder 807 brings the exterior surface of the transfer cylinder 807 having the engraved pattern 814 full of the bonding adhesive 132 proximate to the impression roll 811. The impression roll 811 may be disposed adjacent to the transfer cylinder 807 so that a sheet or film, such as the flexible film 108, placed between the exterior surface of the transfer cylinder 807 and an exterior surface of the impression roll 811 may be compressed between them. The impression roll 811 may be configured to rotate on an axis 819 in the direction indicated by the arrow 821 so that the flexible film 108 may be passed through the transfer assembly 805. As the flexible film 108 passes between the exterior surfaces of the transfer cylinder 807 and the impression roll 811, the second side 136 of the flexible film 108 may be pressed against the exterior of the side surface of the transfer cylinder 807 by the impression roll 811 at a location 823. The compression causes the bonding adhesive 132 drawn into the engraved pattern on the exterior of the side surface of the transfer cylinder 807 to be transferred onto the second side 136 of the flexible film 108 as a portion of the adhesive layer 110.

The conveyor assembly 801 may continue to move the flexible film 108 following passage of the flexible film 108 through the transfer assembly 805. For example, the conveyor assembly 801 may move the flexible film 108, having the bonding adhesive 132 deposited by the transfer assembly 805 thereon, past a curing or drying assembly, such as the curing assembly 825. The curing assembly 825 may be a suitable apparatus configured to cure or dry the bonding adhesive 132 while the conveyor assembly 801 moves the flexible film 108 past the curing assembly 825. Following transfer of the bonding adhesive 132, the bonding adhesive 132 may increase in viscosity, through drying or curing and whether assisted or unassisted, so that the bonding adhesive 132 may resist flow under the application conditions for the medical drape 106. In some embodiments, the flexible film 108 may be configured to pass through another transfer assembly (not shown) to deposit another layer of the bonding adhesive 132 onto the second side 136 so that the bonding adhesive 132 may have a suitable thickness. In these embodiments, the conveyor assembly 801 may be configured to transport the flexible film 108 having the bonding adhesive 132 through another transfer assembly, to operate in reverse to re-feed the flexible film 108 through the transfer assembly 805, or the flexible film 108 may be removed from the conveyor assembly 801 and passed through the transfer assembly 805 again to apply another layer of the bonding adhesive 132.

Once the bonding adhesive 132 of the adhesive layer 110 may be of a suitable thickness, the conveyor assembly 801 may convey the flexible film 108 and the bonding adhesive 132 to a second transfer assembly, such as a transfer assembly 827. The transfer assembly 827 may include a second transfer cylinder, such as transfer cylinder 829, a second well, such as a well 831, a second impression roll, such as an impression roll 833, and a second blade, such as a blade 835. The transfer cylinder 829 may be a cylinder having a side surface with an engraved pattern 830 formed in an exterior of the side surface of the cylinder. The second well 831 may be a suitable container having an interior configured to house or store the sealing adhesive 138. In some embodiments, the adhesive or bonding material may be stored in a liquid form. In other embodiments, the adhesive or bonding material may be stored in a gel form. In the illustrative embodiments, the sealing adhesive 138 may be housed in the second well 831 in a suitably viscous form. In an embodiment, the viscosity range of the sealing adhesive 138 may be between about 100 mPa·s to 10000 mPa·s. The sealing adhesive 138 may be pseudoplastic, that is, the viscosity of the sealing adhesive 138 may be proportional to the applied shear rate and shear thinning so that, at relatively high shear, the sealing adhesive 138 has a low viscosity. The transfer cylinder 829 and the second well 831 may be disposed adjacent to each other so that a lower portion of the transfer cylinder 829 may be submerged in the sealing adhesive 138 during operation of the transfer assembly 827, submerging at least a portion of the engraved pattern 830 of the transfer cylinder 829 in the sealing adhesive 138.

In some embodiments, the second well 831 may be mounted to a floor or other suitable support device and have an upper portion opposite the floor that may be open to the ambient environment. The transfer cylinder 829 may be mounted on an axle 837 so that a lower portion of the transfer cylinder 829 may be disposed within the interior of the second well 831. The transfer cylinder 829 may be rotatable about an axle 837 passing through a center of the transfer cylinder 829. In some embodiments, the transfer cylinder 829 rotates about the axle 837 in the direction indicated by the arrow 839. As the transfer cylinder 829 rotates about the axle 837, a portion of the exterior of the side surface of the transfer cylinder 829 may be submerged in the sealing adhesive 138 housed within the second well 831. While submerged, the sealing adhesive 138 may be drawn into the engraved pattern 830, filling the engraved pattern 830 with the sealing adhesive 138. In some embodiments, the sealing adhesive 138 may be drawn into the engraved pattern 830 by capillary action due to the intermolecular attractive forces between the sealing adhesive 138 and the engraved pattern 830. As the submerged portion rotates out of the second well 831, the submerged portion of the transfer cylinder 829 may rotate past the blade 835. The blade 835 may be a squeegee configured to exert a force on the surface of the transfer cylinder 829 and may be formed of a rubber based material or the like. The blade 835 may be in contact with the exterior side surface so that, as the transfer cylinder 829 rotates out of the second well 831, excess amounts of the sealing adhesive 138 not located in the engraved pattern 830 may be scraped or removed from the exterior surface of the transfer cylinder 829.

Continued rotation of the transfer cylinder 829 brings the exterior of the side surface of the transfer cylinder 829 having the engraved pattern 830 full of the sealing adhesive 138 proximate to the impression roll 833. The impression roll 833 may be disposed adjacent to the transfer cylinder 829 so that a sheet or film, such as the flexible film 108, placed between the exterior side surface of the transfer cylinder 829 and an exterior surface of the impression roll 833 may be compressed between them. The impression roll 833 may be configured to rotate on an axle 841 in the direction indicated by the arrow 843 so that the flexible film 108 may be passed through the transfer assembly 827. As the flexible film 108 passes between the exterior surfaces of the transfer cylinder 829 and the impression roll 833, the second side 136 of the flexible film 108 may be pressed against the exterior of the side surface of the transfer cylinder 829 by the impression roll 833 at a location 834. The compression causes the sealing adhesive 138 drawn into the engraved pattern on the exterior surface of the transfer cylinder 829 to be transferred onto the second side 136 of the flexible film 108 as the sealing adhesive 138 portion of the adhesive layer 110.

The conveyor assembly 801 continues to move the flexible film 108 following passage of the flexible film 108 through the transfer assembly 827. The conveyor assembly 801 may move the flexible film 108, having the adhesive layer 110 printed thereon, past a curing or drying assembly, such as curing assembly 845. The curing assembly 845 may be a suitable apparatus configured to cure or dry the sealing adhesive 138 while the conveyor assembly 801 moves the flexible film 108 past the curing assembly 845. Following transfer of the sealing adhesive 138, the sealing adhesive 138 may increase in viscosity, through drying or curing and whether assisted or unassisted, so that the sealing adhesive 138 may resist flow under the application conditions for the medical drape 106. In some embodiments, the flexible film 108 may be configured to pass through another transfer assembly (not shown) to deposit another layer of the sealing adhesive 138 so that the sealing adhesive 138 may have a suitable thickness. In these embodiments, the conveyor assembly 801 may be configured to transport the flexible film 108 having the sealing adhesive 138 through another transfer assembly, to operate in reverse to re-feed the flexible film 108 through the transfer assembly 827, or the flexible film 108 may be removed from the conveyor assembly 801 and passed through the transfer assembly 827 again to apply another layer of the sealing adhesive 138.

Figure 8C:
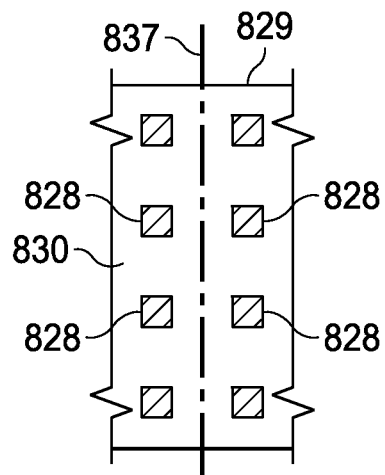
FIG. 8C is a schematic diagram of a portion of an exterior surface of a second transfer cylinder of FIG. 8A.
Figure 8D:
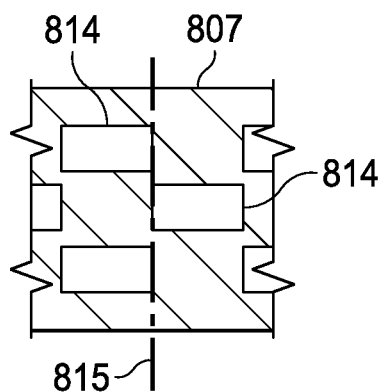
FIG. 8D is a schematic diagram of a portion of another exterior surface of a first transfer cylinder of FIG. 8A.
Figure 8E:
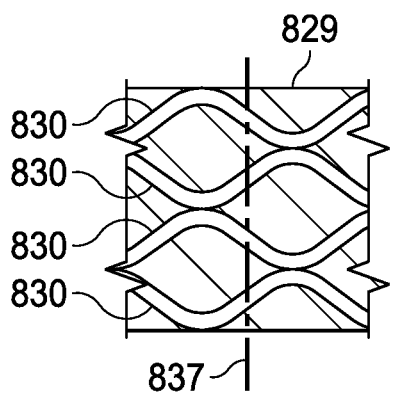
FIG. 8E is a schematic view of a portion of another exterior surface of a second transfer cylinder of FIG. 8A.

FIGS. 8B-8E are schematic diagrams illustrating additional details that may be associated with example embodiments of the transfer cylinder 807 and the second transfer cylinder 827. For example, as shown in FIG. 8B, the engraved pattern 814 may comprise cells aligned on the surface of the transfer cylinder 807 to deposit the cells 715 of the bonding adhesive 132 of the adhesive layer 110 illustrated in FIG. 4A. Similarly, as shown in FIG. 8D, the engraved pattern 814 may comprise cells aligned on the surface of the transfer cylinder 807 to deposit the cells 970 of the bonding adhesive 132 of the adhesive layer 110 illustrated in FIG. 5A. In some embodiments, the speed of the conveyor assembly 801 and the speed of the transfer cylinder 807 may be coordinated to ensure desired deposition of the bonding adhesive 132. As shown in FIG. 8C, the engraved pattern 830 may encompass a substantial portion of the exterior surface of the transfer cylinder 829. Unengraved portions of the exterior surface of the transfer cylinder 829 may form plateaus 828 having a size and shaped substantially equivalent to the cells 715 of the bonding adhesive 132. The plateaus 828 may be aligned on the surface of the transfer cylinder 829 to contact the cells 715 of the bonding adhesive 132 to deposit the sealing adhesive 138 onto portions 717 of the second side 136 of the flexible film 108 as illustrated in FIG. 4B. The plateaus 828 may prevent or limit overlap of the bonding adhesive 132 by the sealing adhesive 138. Similarly, as shown in FIG. 8E, the engraved pattern 830 may comprise strips aligned on the surface of the transfer cylinder 829 to deposit the first strip 939 and the second strip 943 of the sealing adhesive 138 illustrated in FIG. 5B. In some embodiments, the speed of the conveyor assembly 801 and the speed of the transfer cylinder 829 may be coordinated to ensure desired deposition of the sealing adhesive 138 of the adhesive layer 110.

Figure 9A:
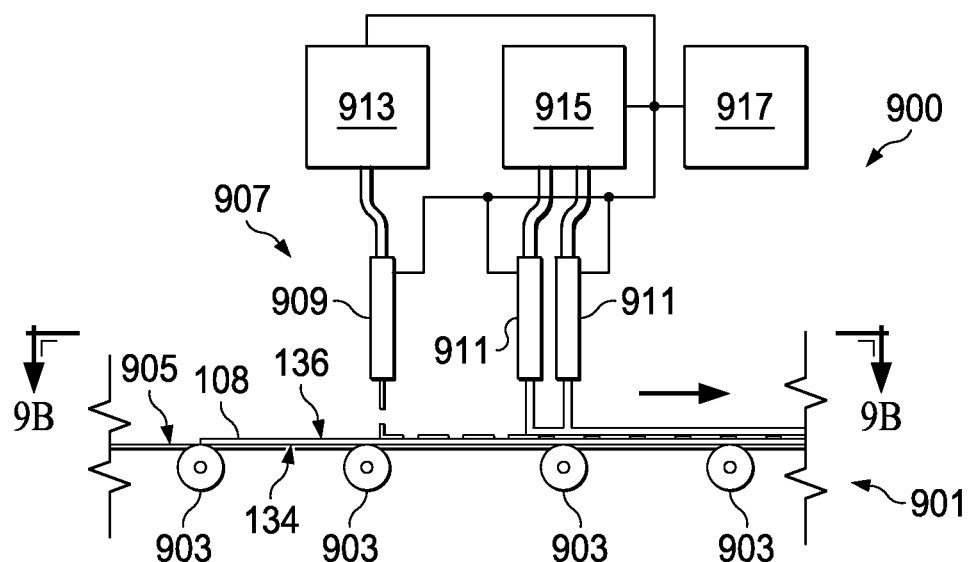
FIG. 9A is a schematic diagram of an illustrative extrusion apparatus for manufacturing the medical drape of FIG. 2.
Figure 9B:
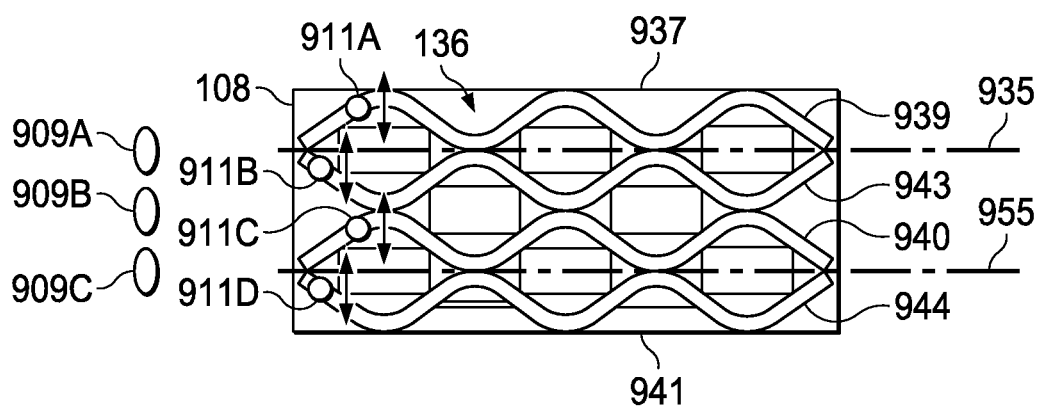
FIG. 9B is a cross sectional view taken along line 9B-9B of FIG. 9A, illustrating the manufacture of an adhesive layer of the medical drape of FIG. 2 using the system of FIG. 9A.

FIGS. 9A and 9B are schematic diagrams of an extrusion apparatus 900 for the manufacturing of the medical drape 106. The flexible film 108 may be provided on a conveyor assembly 901. The conveyor assembly 901 may include one or more rollers 903 on which the flexible film 108 may be disposed. Generally, the rollers 903 may support the flexible film 108 and may be motorized or otherwise powered so that the flexible film 108 may be transported on the conveyor assembly 901. The conveyor assembly 901 may be a conveyor belt, gravity conveyor, bucket conveyor, roller conveyor, chain conveyor, vibrating conveyor, or other device, configured to transport the medical drape 106 through the extrusion apparatus 900. The conveyor assembly 901 may be one or more conveyor systems or a single conveyor system as schematically illustrated in FIG. 9A. The flexible film 108 may be provided to the conveyor assembly 901 in a suitable manner. In some embodiments, the flexible film 108 may be provided to the conveyor assembly 901 in sheets that appear continuous to the conveyor assembly 901 during operation of the conveyor assembly 901. For example, the flexible film 108 may be provided in rolls that may be disposed onto the conveyor assembly 901 and unrolled by the conveyor assembly 901 as the conveyor assembly 901 moves a first end of the flexible film 108 through the extrusion apparatus 900. The flexible film 108 may be disposed on the conveyor assembly 901 so that the first side 134 of the flexible film 108 may be adjacent to an upper surface 905 of a belt of the conveyor assembly 901.

The conveyor assembly 901 may convey the flexible film 108 through an extrusion assembly 907. The extrusion assembly 907 can include one or more bonding adhesive extruders, such as bonding adhesive extruder 909, and one or more sealing adhesive extruders, such as sealing adhesive extruders 911. The bonding adhesive extruder 909 may be coupled to a bonding adhesive supply 913 for the supply of the bonding adhesive 132 to the bonding adhesive extruder 909. Similarly, the sealing adhesive extruders 911 may be coupled to a sealing adhesive supply 915 for the supply of sealing adhesive 138 to the sealing adhesive extruders 911. The extrusion assembly 907 may also include a control system 917 communicatively coupled to the bonding adhesive extruder 909, the sealing adhesive extruders 911, the bonding adhesive supply 913, and the sealing adhesive supply 915 to operate the extrusion assembly 907 as disclosed herein.

The control system 917 may include programmable logic controllers, data processing systems, or the like, configured to receive input from the above listed devices and communicate with those same devices for operation thereof. A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code may be retrieved from bulk storage during execution. The bonding adhesive extruder 909 and the sealing adhesive extruders 911 may be coupled to respective motorized controllers and operable for motion relative to an initial position as disclosed herein. The motorized controllers may be a suitable device configured to receive operative signals or instructions from the control system 917.

The control system 917 may include discreet input/output devices that may be suitable devices such as pneumatic sensors, temperature sensors, or the like configured to communicate signals to the control system 917. Input/output or I/O devices (including but not limited to keyboards, displays, pointing devices, etc.) can be coupled to the system either directly or through intervening I/O controllers. Network adapters, such as a modem or ethernet card, may also be coupled to the control system 917 to enable the control system 917 to become coupled to other data processing systems or remote printers or storage devices through intervening private or public networks.

Each bonding adhesive extruder 909 may be disposed proximate to the upper surface 905 of the conveyor assembly 901. Each bonding adhesive extruder 909 may include a valve and a die configured to extrude an amount of bonding adhesive 132 at a pre-defined interval for a pre-defined duration to deposit the bonding adhesive 132 on the second side 136 of the flexible film 108. FIG. 9B is a schematic diagram representing a portion of a cross section of the extrusion apparatus 900 taken along ling 9B-9B of FIG. 9A. The view of FIG. 9B is taken at a moment in time (t) during operation of the extrusion apparatus 900 where a portion of the bonding adhesive 132 and the sealing adhesive 138 may have been deposited onto the flexible film 108 as described in more detail below. Three bonding adhesive extruders 909 are illustrated in the exemplary embodiments of FIG. 9B, including a first bonding adhesive extruder 909A, a second bonding adhesive extruder 909B, and a third bonding adhesive extruder 909C. Each bonding adhesive extruder 909 may be arranged relative to an adjacent bonding adhesive extruder 909 so that the respective nozzles may be aligned across a width of the flexible film 108. In some embodiments, the first bonding adhesive extruder 909A, the second bonding adhesive extruder 909B, and the third bonding adhesive extruder 909C may coat the width of the flexible film 108 with the bonding adhesive 132 when the first bonding adhesive extruder 909A, the second bonding adhesive extruder 909B, and the third bonding adhesive extruder 909C may be actuated substantially simultaneously. For example, if each of the first bonding adhesive extruder 909A, the second bonding adhesive extruder 909B, and the third bonding adhesive extruder 909C actuated substantially simultaneously, the bonding adhesive 132 would substantially cover the second side 136 of the flexible film 108. In some embodiments, the valves of the first bonding adhesive extruder 909A, the second bonding adhesive extruder 909B, and the third bonding adhesive extruder 909C may be alternatingly actuated by the control system 917 so that a checkerboard pattern may be deposited on the second side 136 of the flexible film 108 as illustrated in FIG. 5A.

Continuing to refer to FIG. 9B, the adhesive layer 110 may be deposited in the following illustrative manner. As the conveyor assembly 901 moves the flexible film 108 past the first bonding adhesive extruder 909A, the second bonding adhesive extruder 909B, and the third bonding adhesive extruder 909C, the control system 917 may actuate the first bonding adhesive extruder 909A and the third bonding adhesive extruder 909C to extrude the bonding adhesive 132 through the respective nozzles for a duration of about three seconds. Following the three second extrusion, the control system 917 may then stop the extrusion of bonding adhesive 132 through the first bonding adhesive extruder 909A and the third bonding adhesive extruder 909C. The control system 917 may then actuate the second bonding adhesive extruder 909B to deposit the bonding adhesive 132 for a duration of about three seconds. The apparatus may then alternatingly actuate the first bonding adhesive extruder 909A and the third bonding adhesive extruder 909C, and the second bonding adhesive extruder 909B. In this manner, the bonding adhesive 132 may be deposited as shown in FIG. 5A to form the first row 971, the second row 972, and the third row 973. The first bonding adhesive extruder 909A, the second bonding adhesive extruder 909B, and the third bonding adhesive extruder 909C may each be operated independently for varying durations to form a desired pattern of the adhesive layer 110 on the second side 136 of the flexible film 108. In other embodiments, more or fewer bonding adhesive extruders 909 may be used and actuated in a suitable manner for a suitable duration to deposit the desired pattern on the second side 136 of the flexible film 108. The extrusion duration may be shorter or longer than three seconds as desired.

Continuing to refer to FIGS. 9A and 9B, the sealing adhesive 138 may be applied in the following illustrative manner. Two pairs of sealing adhesive extruders 911 are shown in FIG. 9B. The first pair of sealing adhesive extruders 911 includes a first sealing adhesive extruder 911A and a second sealing adhesive extruder 911B that may be positioned relative to the reference line 935. In some embodiments, the first sealing adhesive extruder 911A may be configured to move parallel to the width of the flexible film 108 a preset distance from the reference line 935 so that the first sealing adhesive extruder 911A may oscillate between the reference line 935 and the first edge 937 of the flexible film 108. The oscillation may occur in a sinusoidal manner so that, if the flexible film 108 is conveyed past the first sealing adhesive extruder 911A, the first strip 939 of the sealing adhesive 138 may be deposited on the second side 136 of the flexible film 108. Similarly, the second sealing adhesive extruder 911B may be configured to move parallel to the width of the flexible film 108 a preset distance from the reference line 935 so that the second sealing adhesive extruder 911B may oscillate between the reference line 935 and the second edge 941 of the flexible film 108. The oscillation may occur in a sinusoidal manner so that, if the flexible film 108 is carried past the second sealing adhesive extruder 911B, the second strip 943 of the sealing adhesive 138 having sinusoidal wave form may be deposited on the second side 136 of the flexible film 108.

The second pair of sealing adhesive extruders 911 includes a third sealing adhesive extruder 911C and a fourth sealing adhesive extruder 911D that may be positioned relative to the reference line 955. In some embodiments, the third sealing adhesive extruder 911C may be configured to move parallel to the width of the flexible film 108 a preset distance from the reference line 955 so that the third sealing adhesive extruder 911C may oscillate between the reference line 955 and the first edge 937 of the flexible film 108. For example, the oscillation may occur in a sinusoidal manner so that, if the flexible film 108 is carried past the third sealing adhesive extruder 911C, the strip 940 of the sealing adhesive 138 having a sinusoidal wave form may be deposited on the second side 136 of the flexible film 108. Similarly, the fourth sealing adhesive extruder 911D may be configured to move parallel to the width of the flexible film 108 a preset distance from the reference line 955 so that the fourth sealing adhesive extruder 911D may oscillate between the reference line 955 and the second edge 941 of the flexible film 108. The oscillation may occur in a sinusoidal manner so that, if the flexible film 108 is carried past the fourth sealing adhesive extruder 911D, the strip 944 of the sealing adhesive 138 having a sine-wave shape may be deposited on the second side 136 of the flexible film 108. The control system 917 may control the speed of oscillation of the pairs of sealing adhesive extruders 911. In some embodiments, the pairs of sealing adhesive extruders 911 may be actuated by the control system 917 to deposit the first adhesive strip 939, the second adhesive strip 943, the third adhesive strip 940, and the fourth adhesive strip 944 on the second side 136 of the flexible film 108 as illustrated in FIG. 5B.

Figure 10A:
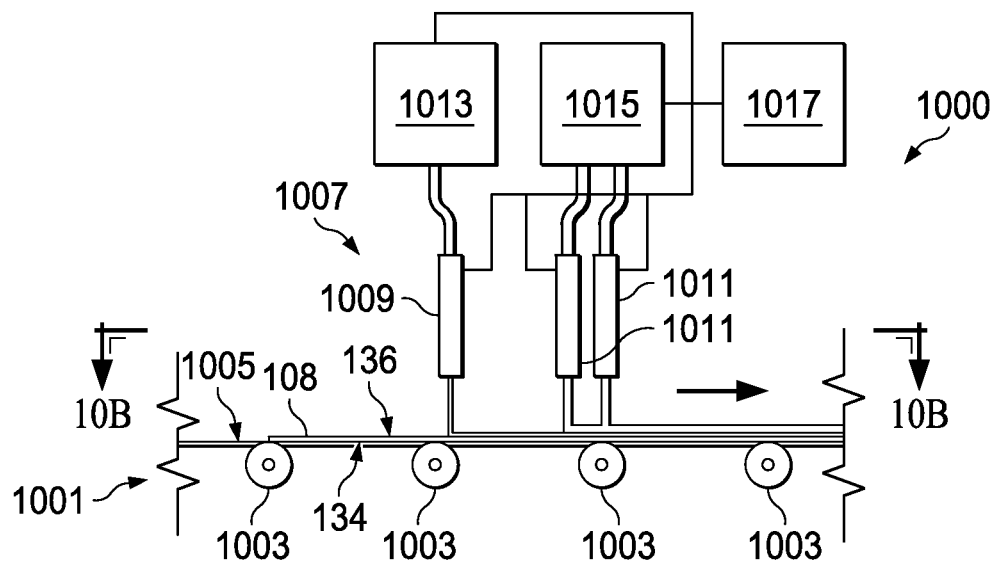
FIG. 10A is a schematic diagram of an illustrative extrusion apparatus for manufacturing the medical drape of FIG. 2.
Figure 10B:
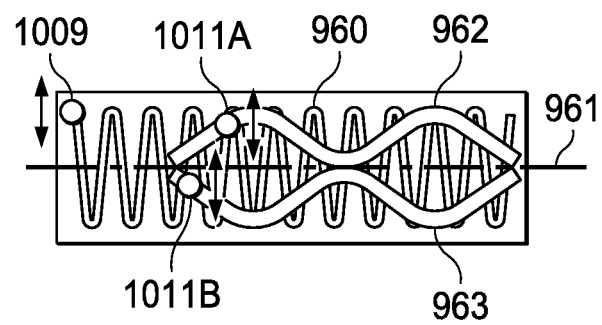
FIG. 10B is a cross sectional view taken along line 10B-10B of FIG. 10A, illustrating the manufacture of an adhesive layer of the medical drape of FIG. 2 using the system of FIG. 10A.

FIGS. 10A and 10B are schematic diagrams of other embodiments of an extrusion apparatus 1000 configured to deposit the adhesive layer 110 of the illustrative medical drape 106 of FIGS. 6A-6C. The extrusion apparatus 1000 may generally include the equipment shown and described with respect to FIGS. 9A and 9B, modified as described below. The reference labels of the components of FIGS. 9A and 9B that may be substantially similar in FIGS. 10A and 10B and analogous components have been indicated by indexing the reference numerals by 100. For example, the extrusion apparatus 1000 may include a conveyor assembly 1001 having rollers 1003, and a belt 1005; and an extrusion assembly 1007 having a bonding adhesive supply 1013, a sealing adhesive supply 1015, and a control system 1017. Each component of the conveyor assembly 1001 and the extrusion assembly 1007 may be substantially similar to the components of the conveyor assembly 901 and the extrusion assembly 907 described above with respect to FIG. 9A. FIG. 10B is a schematic diagram, representative of a portion of a cross-section of the extrusion apparatus 1000 taken along ling 10B-10B of FIG. 10A. The view of FIG. 10B is taken at a moment in time (t) during operation of the extrusion apparatus 1000 where a portion of the bonding adhesive 132 and the sealing adhesive 138 may have been deposited onto the flexible film 108. The sealing adhesive 138 may be deposited on the second side 136 of the flexible film 108 in a manner similar to that described with respect to FIGS. 9A and 9B, to deposit the first strip 962 and the second strip 963 of FIG. 10B. The bonding adhesive extruder 1009 may be an oscillating extruder 1009. The oscillating extruder 1009 may be oscillate about a reference line 961. The oscillation may occur in a sinusoidal manner so that, if the flexible film 108 is carried past the oscillating extruder 1009, a strip 960 of the bonding adhesive 132 having an oscillating wave form may be deposited on the second side 136 of the flexible film 108. In some embodiments, the period of oscillation for the oscillating extruder 1009 may be shorter than the period of oscillation for the first sealing adhesive extruder 1011A and the second sealing adhesive extruder 1011B of the first pair of sealing adhesive extruders 1011.

The manufacturing apparatuses described above with respect to specific embodiments of the medical drape 106 may be used to manufacture the embodiments of FIGS. 4A-6C, as well as variations thereof. In some embodiments, the rheology of the adhesives may be modified in a suitable manner to reduce the amount of flow between the process of deposition onto the flexible film 108 by the screen depositing, transfer, or extrusion processes and curing or drying to prevent adhesive migration onto undesired areas of the flexible film 108. In still other embodiments, the flexible film 108 may be rotated or inverted repeatedly during the drying or curing process to limit adhesive migration on the flexible film 108.

In still other embodiments, the adhesives may be mixed with blowing or expanding agents, for example organic and inorganic low temperature boiling point liquids. The blowing or expanding agents allow for the adhesives to expand under the application of heat or light to increase the thickness of the adhesive following deposition by one of the above described processes. The blowing or expanding agents may reduce the amount of adhesive needed and decrease the cost of production and the cost of the resulting medical drape 106. In some embodiments, the application of heat or light may be delayed until application of the medical drape 106 to the epidermis 112 of the patient 104 so that the contact area with the patient's epidermis 112 may increase as the bonding adhesive 132 and the sealing adhesive 138 warm by contact with the patient's epidermis 112. The application of light or heat following application of the medical drape 106 to the epidermis 112 can provide a better seal for some embodiments of the medical drape 106 to the epidermis 112.

Using the above described apparatuses to manufacture patterned adhesive layers onto a drape can provide numerous advantages. For example, the amount of overlap between adhesive layers can be decreased and allow greater control of the application of the adhesive to the drape. The amount of adhesive needed to achieve the desired results can be decreased, providing a cost savings over prior art manufacturing methods. A hybrid medical drape 106 having two adhesive types may be produced that allows for an increased evaporation efficiency. Areas of the flexible film 108 uncovered by either the bonding adhesive 132 or the sealing adhesive 138 can also allow for high fluid diffusion and evaporation over coated regions. High fluid diffusion and evaporation can increase the ability of the medical drape 106 to manage fluid balance with healthy skin. High fluid diffusion and evaporation can also increase the ability of the medical drape 106 to evaporate fluid from underlying structures, such as the manifold 122. When combined with system 100 of FIG. 1, the medical drape 106 may increase the diffusion efficiency of the system 100. In addition, use of a broader range of combinations of different adhesives may be obtained. Still further, the process of manufacturing the medical drape 106 may be simplified, further decreasing the cost of production of the medical drape 106.

Although certain structures and their advantages have been disclosed in the context of certain illustrative, non-limiting embodiments, it should be understood that various changes, substitutions, permutations, and alterations can be made without departing from the scope of the appended claims. It will be appreciated that features that may be described in connection to one embodiment may also be applicable to other embodiments. It will also be understood that the benefits and advantages described above may relate to one embodiment or may relate to several embodiments. It will further be understood that reference to "an" item refers to one or more of those items.

The steps of the methods described herein may be carried out in a suitable order, or simultaneously where appropriate.

Where appropriate, aspects of the embodiments described above may be combined with aspects of the other embodiments described to form further examples having comparable or different properties and addressing the same or different problems.

It will be understood that the embodiments described herein are given by way of example only and that various modifications may be made by those skilled in the art. The above specification, examples and data provide a complete description of the structure and use of exemplary embodiments. Although various embodiments have been described above with a certain degree of particularity, or with reference to one or more individual illustrations, those skilled in the art could make numerous alterations to the example embodiments without departing from the scope of the claims.

We claim:

1. A medical drape comprising:
 a flexible film;
 a first adhesive disposed on a first portion of the flexible film in a first pattern, the first adhesive comprising a bonding adhesive, wherein the first pattern comprises:
  a first row of the first adhesive adjacent to an edge of the flexible film, the first row having a plurality of cells, each cell separated from adjacent cells of the first row,
  a second row of the first adhesive separated from the edge of the flexible film, the second row having a plurality of cells offset from the cells of the first row, each cell separated from adjacent cells of the second row; and
 a second adhesive disposed on a second portion of the flexible film in a second pattern, the second adhesive comprising a sealing adhesive, the second pattern registered with the first pattern so that the first portion and the second portion cover substantially different portions of the flexible film, the first adhesive and the second adhesive disposed on a same side of the flexible film and the second adhesive having a thickness greater than a thickness of the first adhesive, wherein the second pattern comprises one or more periodic wave-shaped strips of the second adhesive, the periodic wave-shaped strips having maximum and minimum amplitudes that correspond with medial portions of the cells of the first and the second rows, respectively, so that the periodic wave-shaped strips enclose the cells of the first and the second rows that propagate parallel to the edge of the flexible film.

2. The medical drape of claim 1, wherein the flexible film comprises a polyurethane film.

3. The medical drape of claim 1, wherein the flexible film has a moisture vapor transfer rate between 300 g/m2/24 hours to 14,400 g/m2/24 hours.

4. The medical drape of claim 3, wherein the flexible film has a moisture vapor transfer rate of 1000 g/m2/24 hours.

5. The medical drape of claim 1, wherein the first adhesive is an acrylic adhesive, and the second adhesive is a silicone adhesive.

6. The medical drape of claim 1, wherein the second adhesive has a tackiness less than a tackiness of the first adhesive.

7. The medical drape of claim 1, wherein the first adhesive has a thickness between 30 microns and 65 microns, and the second adhesive has a thickness between 100 microns and 400 microns.

8. The medical drape of claim 1, wherein the first portion and the second portion cover less than a side of the flexible film.

* * * * *